United States Patent
Op Den Camp et al.

(10) Patent No.: US 11,576,318 B2
(45) Date of Patent: *Feb. 14, 2023

(54) METHOD FOR THE PRODUCTION OF HAPLOID AND SUBSEQUENT DOUBLED HAPLOID PLANTS

(71) Applicant: Keygene N.V., Wageningen (NL)

(72) Inventors: Rik Hubertus Martinus Op Den Camp, Wageningen (NL); Peter Johannes Van Dijk, Wageningen (NL); Anthony Gallard, Wageningen (NL)

(73) Assignee: KEYGENE N.V., Wageningen (NL)

( * ) Notice: Subject to any disclaimer, the term of this patent is extended or adjusted under 35 U.S.C. 154(b) by 114 days.

This patent is subject to a terminal disclaimer.

(21) Appl. No.: 17/106,463

(22) Filed: Nov. 30, 2020

(65) Prior Publication Data

US 2021/0076584 A1 Mar. 18, 2021

Related U.S. Application Data

(63) Continuation of application No. 15/763,710, filed as application No. PCT/NL2016/050683 on Oct. 3, 2016, now Pat. No. 10,849,289.

(30) Foreign Application Priority Data

Oct. 2, 2015 (NL) ...................... 2015549

(51) Int. Cl.
*A01H 1/08* (2006.01)
*C07K 14/415* (2006.01)
*C12N 15/82* (2006.01)

(52) U.S. Cl.
CPC ............ *A01H 1/08* (2013.01); *C07K 14/415* (2013.01); *C12N 15/8218* (2013.01); *C12N 15/8241* (2013.01); *C12N 15/8261* (2013.01); *C12N 15/8287* (2013.01); *Y02A 40/146* (2018.01)

(58) Field of Classification Search
CPC ....................................... A01H 1/08
See application file for complete search history.

(56) References Cited

U.S. PATENT DOCUMENTS 10,849,289 B2 * 12/2020 Op Den Camp .. C12N 15/8261

FOREIGN PATENT DOCUMENTS

| WO | WO-2008/097791 A2 | 8/2008 |
| WO | WO-2011/044132 A1 | 4/2011 |
| WO | WO-2014/110274 A2 | 7/2014 |

OTHER PUBLICATIONS

GenBank: TMX01996.1 Jun. 5, 2019 (Year: 2019).*
Gen Bank Accession BX663207.1, Apr. 2004; Arabidopsis flanking sequence GK-710G06-022961. (Year: 2004).*
Gene ID 816179 for AT2G16780.1 Msi2 updated Aug. 28, 2022. (Year: 2022).*
DATABASE UniProt [Online], "SubName: Full=Uncharacterized protein {ECO:0000313|EnsemblPlants:Solyc01g111590.2.1}", retrieved from EBI accession No. UNIPROT:K4B421 Database accession No. K4B421 sequence fully comprises present SEQ ID No. 6, Nov. 28, 2012, abstract.
Gen Bank Accession BX663107.1, Apr. 2004; Arabidopsis thaliana T-DNA flanking sequence GK-710G06-0022961.
International Search Report issued in International Patent Application No. PCT/NL2016/050683, dated Jan. 13, 2017.
Ravi et al., "A haploid genetics toolbox for *Arabidopsis thaliana*", Nature Communications, Oct. 2014, pp. 1-8.
Ravi et al., "Haploid plants produced by centromere-mediated genome elimination", Nature, Mar. 2010, vol. 464, pp. 615-620.
Tair Polymorphism Search Results At2G16780; www.arabidopsis.org; 2 pages. (Year: 2019).

* cited by examiner

*Primary Examiner* — Russell Kallis
(74) *Attorney, Agent, or Firm* — Sunit Talapatra; Foley & Lardner LLP

(57) ABSTRACT

It was found that plants with loss of functional Msi2 protein due to a nucleotide polymorphism resulting in the introduction of a premature stop codon in the Msi2 protein, are able to induce haploid offspring after a cross to or with a wild type plant comprising a functional Msi2 protein. The invention relates to generation of haploid and doubled haploid plants.

14 Claims, 1 Drawing Sheet

Specification includes a Sequence Listing.

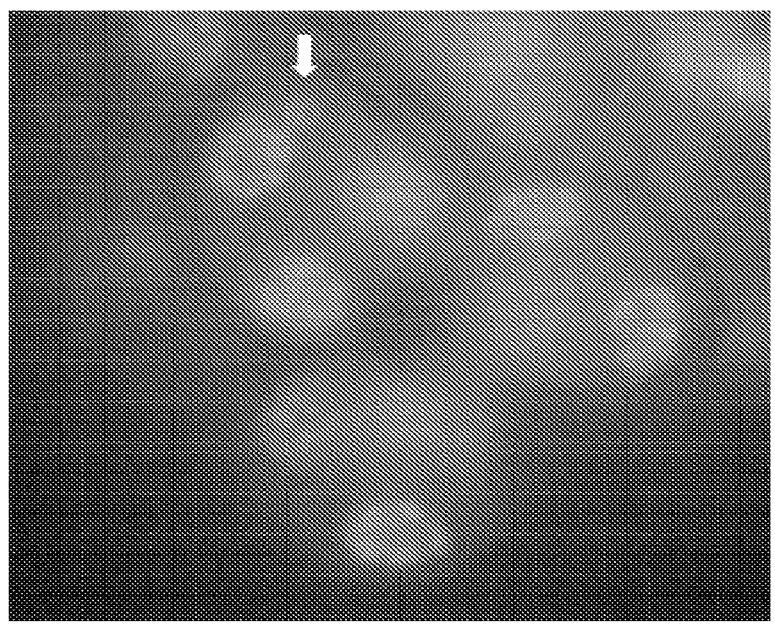

METHOD FOR THE PRODUCTION OF HAPLOID AND SUBSEQUENT DOUBLED HAPLOID PLANTS

CROSS-REFERENCE TO RELATED APPLICATIONS

This application is a continuation of U.S. patent application Ser. No. 15/763,710 filed Mar. 27, 2018 which is the national phase entry of International Patent Application No. PCT/NL2016/050683, filed Oct. 3, 2016, published on Apr. 6, 2017 as WO 2017/058023 A1, which claims priority to Netherlands Patent Application No. 2015549, filed Oct. 2, 2015. The contents of these applications are herein incorporated by reference in their entirety.

SEQUENCE LISTING

The instant application contains a Sequence Listing which has been submitted in ASCII format via EFS-WEB and is hereby incorporated by reference in its entirety. The ASCII copy, created on Sep. 26, 2018, is named 085342-2401SequenceListing.txt and is 29 KB.

FIELD OF THE INVENTION

The disclosure relates to the field of agriculture. In particular, the disclosure relates to the production of haploid and subsequent doubled haploid plants.

BACKGROUND OF THE INVENTION

A high degree of heterozygosity in breeding material can make plant breeding and selection for beneficial traits a very time consuming process. Extensive population screening, even with the latest molecular breeding tools, is both laborious and costly.

The creation of haploid plants followed by chemical or spontaneous genome doubling is an efficient way to solve the problem of high heterozygosity. Such doubled haploids bypass at least 7 generations of selfing otherwise needed to reduce the heterozygosity to an acceptable level. Haploid plants can be produced in some crops by microspore culture. However, this is costly and time-consuming. More importantly, in many crops microspore culture methods do not work. In some crop species, (doubled) haploid plants can be obtained by parthenogenesis of the egg cell or by elimination of one of the parental genomes. However, these methods are also restricted to a few selected crops and the production rates of doubled haploid plants are low.

WO2011/044132 discloses methods of producing haploid plants. One of the methods employed is inactivating or knocking out CenH3 protein. This was done by adding an N-terminal GFP to the CenH3 protein, thereby creating GFP-CenH3. This is also called a "tailswap". The tailswap was sufficient to induce uni-parental genome elimination upon a cross to a plant without such modified N-terminal part of the CenH3 protein. The uni-parental genome elimination resulted in the production of a haploid plant. So far this process has only been demonstrated in the model plant Arabidopsis thaliana and not in crop plants. Additionally, when another artificial construct, which consisted of a different trans-genetically modified N-terminal part of the CenH3 protein, was introduced in a plant with a genetic background lacking the endogenous CenH3, it appeared that this did not resulted in uni-parental genome elimination and subsequent production of a haploid plant (WO 2014/110274). Therefore it remains elusive which modifications of the CenH3 protein are sufficient for uni-parental genome elimination.

Thus, there remains a need in the art for methods that allow efficient generation of haploid plants which can subsequently be doubled, to produce doubled haploid plants. With doubled haploid production systems, homozygosity is achieved in one generation.

SUMMARY OF THE INVENTION

The present inventors have now found that *Solanum lycopersicum* plants with loss of functional Msi2 protein due to a unique single nucleotide polymorphism resulting in a K to STOP codon amino acid modification at position 126 in the *Solanum lycopersicum* Msi2 protein, are able to induce haploid offspring after a cross to or with a wild type plant comprising a functional Msi2 protein. A single nucleotide polymorphism resulting in a K to M amino acid modification in the Msi2 protein was found to be non-disruptive by computational methods (SIFT, Kumar P, Henikoff S, Ng PC. (2009) Predicting the effects of coding non-synonymous variants on protein function using the SIFT algorithm. Nat Protoc; 4(7):1073-81). In line with these models, the latter amino acid modification did not induce haploid offspring after a cross to or with a wild type plant lacking that particular K to M acid modification in the Msi2 protein. Reciprocal control cross with a synonymous single nucleotide polymorphism, not changing the amino acid sequence (Msi2D337D), did not yield any haploid offspring.

In a first aspect, the present invention pertains to an Msi2 protein of plant origin comprising a loss-of-function mutation.

Said mutation may be present in a WD40 repeat and/or in a CAF1C domain.

Said Msi2 protein may be encoded by a plant Msi2 protein-encoding polynucleotide having a loss-of-function mutation, which protein, when present in a plant in the absence of its endogenous Msi2 protein, allows generation of some haploid progeny, or progeny with aberrant ploidy, when said plant is crossed with a wild-type plant.

Said Msi2 protein may be derived from a polypeptide comprising the amino acid sequence of SEQ ID NO:1 or 10, or a variant thereof having at least 70%, more preferably at least 80%, even more preferably at least 90%, yet even more preferably at least 95%, most preferably at least 98% or 99% sequence identity to the amino acid sequence of SEQ ID NO:1 or 10, said protein being encoded by a plant Msi2 protein-encoding polynucleotide having a loss-of-function mutation, which protein, when present in a plant in the absence of its endogenous Msi2 protein, allows generation of some haploid progeny, or progeny with aberrant ploidy, when said plant is crossed with a wild-type plant.

Said Msi2 protein may be derived from a polypeptide comprising the amino acid sequence of SEQ ID NO:2 or 3, or a variant thereof having at least 70%, more preferably at least 80%, even more preferably at least 90%, yet even more preferably at least 95%, most preferably at least 98% or 99% sequence identity to the amino acid sequence of SEQ ID NO:2 or 3, said protein being encoded by a plant Msi2 protein-encoding polynucleotide having a loss-of-function mutation, which protein, when present in a plant in the absence of its endogenous Msi2 protein, allows generation of some haploid progeny, or progeny with aberrant ploidy, when said plant is crossed with a wild-type plant. For example, at least 0.1, 0.5, 1 or 5% of the progeny produced is haploid, or has an aberrant ploidy, or is doubled-haploid.

The loss-of-function mutation may introduce a premature stop codon that causes truncation of the protein. For example, the protein may be truncated after the amino acid residue at position 125 in SEQ ID NO:2, 3 or 10, or after the amino acid residue at position 123 in SEQ ID NO:1.

In an embodiment, the Msi2 protein comprises the amino acid sequence of SEQ ID NO:6 or consists of the amino acid sequence of SEQ ID NO:6.

In an embodiment, the Msi2 protein may be encoded by a nucleic acid molecule comprising the nucleic acid sequence of SEQ ID NO:4 or 9.

The Msi2 protein may be encoded by a polynucleotide comprising a loss-of-function mutation that is derived from a polynucleotide encoding an endogenous Msi2 protein using targeted nucleotide exchange or by applying an endonuclease.

In another aspect, the invention provides a nucleic acid molecule encoding the Msi2 protein taught herein.

Also, the invention provides a nucleic acid molecule comprising the nucleic acid sequence of SEQ ID NO:5, 7, or 8, or a variant thereof having at least 70%, more preferably at least 80%, even more preferably at least 90%, yet even more preferably at least 95%, most preferably at least 98% or 99% sequence identity to the nucleic acid sequence of SEQ ID NO:5, 7 or 8, in which one or more nucleotides of the nucleic acid sequence of SEQ ID NO:5, 7 or 8 are modified such that the nucleic acid molecule encodes a Msi2 protein comprising a loss-of-function mutation.

The invention also provides a nucleic acid molecule comprising the nucleic acid sequence of SEQ ID NO:5, 7, or 8, or a variant thereof having at least 70%, more preferably at least 80%, even more preferably at least 90%, yet even more preferably at least 95%, most preferably at least 98% or 99% sequence identity to the nucleic acid sequence of SEQ ID NO:5, 7, or 8, in which one or more nucleotides are modified such that a premature stop codon is introduced and the nucleic acid molecule encodes a truncated Msi2 protein.

In an embodiment, one or more nucleotides at positions 376, 377 and/or 378 of the nucleic acid sequence of SEQ ID NO:5 or 7, or one or more nucleotides at positions 685, 686 and/or 687 of the nucleic acid sequence of SEQ ID NO:8, are modified such that a stop codon is introduced and the nucleic acid molecule encodes a polypeptide comprising an amino acid sequence that is truncated after the amino acid residue corresponding to position 125 in SEQ ID NO:2 or 3.

Also taught is a nucleic acid molecule comprising the nucleic acid sequence of SEQ ID NO:4 or 9.

The nucleic acid molecule taught herein may be an isolated nucleic acid, a genomic nucleic acid, or a cDNA.

The invention further provides a chimeric gene comprising the nucleic acid molecule taught herein, and a vector comprising the nucleic acid molecule taught herein or the chimeric gene taught herein.

The invention further pertains to a host cell comprising a nucleic acid molecule taught herein, a chimeric gene taught herein, or a vector as taught herein.

Said host cell may be a plant cell, including a protoplast, preferably a tomato plant cell.

Also disclosed is a plant, seed, or plant cell comprising the nucleic acid molecule as taught herein, a chimeric gene as taught herein, or a vector as taught herein.

In an embodiment, the endogenous Msi2 protein is not expressed in said plant, seed, or plant cell.

The invention also relates to a plant, seed, or plant cell wherein the endogenous Msi2 protein is not expressed, for example, wherein the endogenous Msi2 gene is knocked out.

In an embodiment, said plant, seed, or plant cell is not an *Arabidopsis thaliana* plant, seed, or plant cell.

Said plant, seed, or plant cell may be a *Solanum* plant, seed, or plant cell, preferably a *Solanum lycopersicum* plant, seed, or plant cell.

The invention is further concerned with a method for making a plant, seed, or plant cell as taught herein, said method comprising the steps of:
a) modifying an endogenous Msi2 gene within a plant cell to obtain a mutated Msi2 gene encoding an Msi2 protein as taught herein, or modifying an endogenous Msi2 gene within a plant cell in order to knock out expression of endogenous Msi2 protein within a plant cell;
b) selecting a plant cell comprising the mutated Msi2 gene, or a plant cell in which expression of said endogenous Msi2 protein is knocked out; and
c) optionally, regenerating a plant from said plant cell.

The invention is also directed to a method for making a plant, seed, or plant cell as taught herein, said method comprising the steps of:
a) transforming a plant cell with a nucleic acid molecule as taught herein, a chimeric gene as taught herein, or a vector as taught herein, or transforming a plant cell with a nucleic acid molecule in order to knock out expression of an endogenous Msi2 protein;
b) optionally, additionally modifying an endogenous Msi2 gene within a plant cell in order to knock out expression of endogenous Msi2 protein within said plant cell;
c) selecting a plant cell comprising the nucleic acid molecule as taught herein, a chimeric gene as taught herein, or a vector as taught herein, and/or a plant cell in which expression of endogenous Msi2 protein is knocked out; and
d) optionally, regenerating a plant from said plant cell.

In another aspect, the invention provides for a method of generating a haploid plant, a plant with aberrant ploidy, or a doubled haploid plant, said method comprising the steps of:
a) crossing a plant expressing an endogenous Msi2 protein to the plant as taught herein, wherein the plant as taught herein lacks expression of endogenous Msi2 protein at least in its reproductive parts and/or during embryonic development;
b) harvesting seed;
c) growing at least one seedling, plantlet or plant from said seed; and
d) selecting a haploid seedling, plantlet or plant, a seedling, plantlet or plant with aberrant ploidy, or a doubled haploid seedling, plantlet or plant.

The invention also relates to a method of generating a doubled haploid plant, said method comprising the steps of:
a) crossing a plant expressing an endogenous Msi2 protein to the plant as taught herein, wherein the plant as taught herein lacks expression of endogenous Msi2 protein at least in its reproductive parts and/or during embryonic development;
b) selecting a haploid plant; and
c) converting said haploid plant into a doubled haploid plant.

The conversion in step c) may be performed by treatment with colchicine.

The plant expressing an endogenous Msi2 protein may be an F1 plant.

The plant expressing an endogenous Msi2 protein may be a pollen parent of the cross, or may be an ovule parent of the cross.

The cross may be performed at a temperature in the range of about 24 to about 30° C., preferably in the range of about 26 to about 28° C.

The invention further relates to use of the nucleic acid molecule as taught herein for producing a haploid inducer line.

Also, the invention is directed to a *Solanum lycopersicum* plant, seed, or plant cell comprising the nucleic acid molecule as taught herein, the chimeric gene as taught herein, or the vector as taught herein.

Further, a *Solanum lycopersicum* plant, seed, or plant cell comprising a nucleic acid molecule encoding a polypeptide comprising the amino acid sequence of SEQ ID NO:6, is taught herein.

Also, a *Solanum lycopersicum* plant, seed, or plant cell comprising the nucleic acid molecule of SEQ ID NO:4 or 9 is taught herein.

In yet another aspect, a *Solanum lycopersicum* plant, seed or plant cell comprising a nucleic acid molecule that encodes a Msi2 protein as taught herein, is provided.

Also, a *Solanum lycopersicum* plant, seed, or plant cell which lacks expression of functional Msi2 protein; optionally, wherein an Msi2 protein comprising a loss-of-function mutation is expressed, is taught herein.

The *Solanum lycopersicum* plant as taught herein may be used for producing a haploid *Solanum lycopersicum* plant, and/or for producing a doubled haploid *Solanum lycopersicum* plant.

The *Solanum lycopersicum* plant taught herein may lack expression of endogenous Msi2 protein at least in its reproductive parts and/or during embryonic development.

In a final aspect, the invention is directed to a method of generating a haploid or doubled haploid plant, said method comprising the step of identifying a plant expressing an endogenous Msi2 protein and a plant as taught herein, wherein the plant as taught herein lacks expression of endogenous Msi2 protein at least in its reproductive parts and/or during embryonic development.

The crossing methods as taught herein do not comprise sexually crossing the whole genomes of said plants.

Definitions

The term "Msi2" refers to Musashi RNA-binding protein 2. It is a WD-40 repeat-containing protein. WD-40 repeats (also known as WD or beta-transducin repeats) are short ~40 amino acid motifs, often terminating in a Trp-Asp (W-D) dipeptide. WD40 repeats usually assume a 7-8 bladed beta-propeller fold, but proteins have been found with 4 to 16 repeated units, which also form a circularized beta-propeller structure. WD-repeat proteins are a large family found in all eukaryotes and are implicated in a variety of functions ranging from signal transduction and transcription regulation to cell cycle control and apoptosis. Repeated WD40 motifs act as a site for protein-protein interaction, and proteins containing WD40 repeats are known to serve as platforms for the assembly of protein complexes or mediators of transient interplay among other proteins. The specificity of the proteins is determined by the sequences outside the repeats themselves. Msi2 is thought to be an RNA binding protein that regulates the expression of target mRNAs at the translation level. In *Arabidopsis* spp., several WD40-containing proteins act as key regulators of plant-specific developmental events. An *Arabidopsis thaliana* Msi2 (At2g16780) T-DNA insertion mutant and Msi2-over-expressing transgenic plant were reported to have the same phenotype as wild-type. The expression of the Msi2 gene in wild-type could not be induced by drought, salt, high temperature, low temperatures, mannitol, ABA, GA, salicylic acid and jasmonic acid. A localization study using a fusion protein consisting of the full length of Msi2 cDNA and GFP under the control of 35S promoter revealed that fluorescence was detected in both the cytosol and nucleus. The exact role of Msi2 in the plant is yet unknown.

A "mutation" is a permanent change of the nucleotide sequence of the genome of an organism, virus, or extrachromosomal DNA or other genetic elements. Mutations result from damage to DNA which is not repaired or to RNA genomes (typically caused by radiation or chemical mutagens), errors in the process of replication, or from the insertion or deletion of segments of DNA by mobile genetic elements. Mutations may or may not produce discernible changes in the observable characteristics (phenotype) of an organism. A mutation can result in several different types of change in sequences. Mutations in genes can either have no effect, alter the product of a gene, or prevent the gene from functioning properly or completely. Mutations can also occur in non-genic regions.

A "loss-of-function mutation" in a protein in the context of the present invention refers to a mutation in a protein that causes loss of its function. A "loss-of-function mutation" in a polynucleotide refers to a mutation in a polynucleotide encoding a protein that causes loss-of-function of said protein. A protein may still be produced from the polynucleotide comprising the loss-of-function mutation, but the protein can no longer perform its function or cannot perform its function effectively.

A "loss-of-expression mutation" results in loss of expression of the mutated gene or the product encoded by said mutated gene.

A "loss-of-function Msi2 protein" is an Msi2 protein that comprises a loss-of-function mutation. Said loss-of-function Msi2 protein, when present in a plant in the absence of its endogenous Msi2 protein, allows generation of some haploid progeny, or progeny with aberrant ploidy, when said plant is crossed with a wild-type plant, preferably a wild-type plant of the same species. A loss-of-function Msi2 protein may also become non-functional or less functional by using inhibitors of the protein, such as an antibody specifically binding the Msi2 protein, or other Msi2 inhibitors, e.g. proteins that block, prevent or reduce the activity of an endogeous Msi2 protein, or chemical inhibitors such as ions, or metals, or scavenging of co-factors. For example, an antibody specifically binding Msi2 protein may be expressed simultaneously with said Msi2 protein, thereby reducing its specific activity. The Msi2 protein function may be impaired, or the Msi2 protein may be less functional than the endogenous Msi2 protein.

A "loss-of-function Msi2 protein-encoding polynucleotide" refers to a non-endogenous, mutated Msi2 protein-encoding polynucleotide that encodes an Msi2 protein comprising a loss-of-function mutation, which, when present in a plant in the absence of its endogenous Msi2 protein-encoding polynucleotide, allows generation of some haploid progeny, or progeny with aberrant ploidy, when said plant is crossed with a wild-type plant, preferably a wild-type plant of the same species. A loss-of-function mutation includes a frame-shift mutation.

The term "endogenous" as used in the context of the present invention in combination with protein, gene, or polynucleotide means that said protein, gene or polynucleotide originates from the plant in which it is still contained. Often an endogenous gene will be present in its normal genetic context in the plant.

The term "gene" as used herein refers to a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites.

The term "haploid inducer line" used in the context of the present disclosure refers to a plant line which differs in at least one single nucleotide polymorphism from the non-inducer line. When an haploid inducer line is crossed, either used as female or as pollen donor, it results in uni-parental genome elimination of the haploid inducer line's genome.

The term "uni-parental genome elimination" as used herein refers to the effect of losing all the genetic information, meaning all chromosomes, of one parent after a cross irrespective of the direction of the cross. This occurs in such way that the offspring of such cross will only contain chromosomes of the non-eliminated parental genome. The genome which is eliminated always has the origin in the haploid inducer parent.

A "doubled haploid" is a genotype formed when haploid cells undergo chromosome doubling. It may be produced by induced or spontaneous chromosome doubling from haploid cells. For diploid plants, the haploid cells are monoploid, and the term "doubled monoploid" may also be used for the doubled haploids.

A "frame-shift mutation" (also called a framing error or a reading frame shift) is a genetic mutation caused by indels (insertions or deletions) of a number of nucleotides that is not evenly divisible by three in a nucleotide sequence. Due to the triplet nature of gene expression by codons, the insertion or deletion can change the reading frame (the grouping of the codons), resulting a completely different translation of the template. The earlier in the sequence the deletion or insertion occurs, the more altered the protein product is. A frame shift mutation will in general cause the reading of the codons after the mutation to code for different amino acids, but there may be exceptions resulting from the redundancy in the genetic code. Furthermore, the stop codon in the original sequence will not be read, and an alternative stop codon may result at an earlier or later stop site. The protein product may be abnormally short or abnormally long.

The terms "polynucleotide", "nucleic acid molecule", and "nucleic acid" are used interchangeably herein.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithms such as FASTA, BLAST, etc.

A "host cell" or a "recombinant host cell" or "transformed cell" are terms referring to a new individual cell (or organism) arising as a result of introduction of at least one nucleic acid molecule, especially comprising a chimeric gene encoding a desired protein. The host cell is preferably a plant cell or a bacterial cell. The host cell may contain the nucleic acid molecule or chimeric gene as an extra-chromosomally (episomal) replicating molecule, or more preferably, comprises the nucleic acid molecule or chimeric gene integrated in the nuclear or plastid genome of the host cell.

As used herein, the term "plant" includes plant cells, plant tissues or organs, plant protoplasts, plant cell tissue cultures from which plants can be regenerated, plant calli, plant cell clumps, and plant cells that are intact in plants, or parts of plants, such as embryos, pollen, ovules, fruit (e.g. harvested tomatoes), flowers, leaves, seeds, roots, root tips and the like.

In this document and in its claims, the verb "to comprise" and its conjugations is used in its non-limiting sense to mean that items following the word are included, but items not specifically mentioned are not excluded. It encompasses the verbs "to essentially consist of" and "to consist of".

In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

DETAILED DESCRIPTION OF THE INVENTION

Mode of Action of the Invention

It is believed that plants in which expression of functional Msi2 protein is impaired and/or functionality of the Msi2 protein is impaired resulting in the absence or reduced presence of functional Msi2 protein, gives such plant the haploid inducer phenotype. When said plant is crossed with a sexually compatible wild-type plant, preferably a wild-type plant of the same species, generation of some haploid progeny, or progeny with aberrant ploidy, is induced at relatively high frequency. The percentage of haploid progeny or progeny with aberrant ploidy that is generated using such plant can, for instance, be at least 0.1, 0.5, 1, 5, 10, 20%, or more.

Impaired expression of a functional Msi2 protein may mean that the expression of the Msi2 gene is impaired, and/or that expression of the Msi2 gene is normal but translation of the transcribed mRNA is inhibited or prevented (for example by RNA interference).

Impaired expression of functional Msi2 protein at the transcriptional level can be the result of the introduction of one or more mutations in transcription regulation sequences, including promoters, enhancers, or initiation, termination or intron splicing sequences. These sequences are generally located 5' of, or 3' of, or within the coding sequence of the gene or genes coding for Msi2 protein. Alternatively or additionally, impaired expression of functional Msi2 protein can also be achieved by deletion, substitution, rearrangement or insertion of nucleotides in the coding region of the endogenous Msi2 gene or genes. For example, in the coding region, nucleotides may be substituted, inserted or deleted leading to the introduction of one, two or more premature stop codons. Also, insertion, deletion, rearrangement or substitution can lead to modifications in the amino acid sequence encoded, and thereby provide for impaired expression of functional Msi2 protein. Large parts of the Msi2 gene(s) may be removed, for example, at least 10%, 20%, 30%, 40%, 50%, 60%, 70%, 80%, 90% or even 100% of the (coding region) of the Msi2 gene(s) may be removed from the DNA present in the plant, thereby impairing expression of functional Msi2 protein.

Alternatively, one, two, three or more nucleotides may be introduced into the Msi2 gene(s), leading to, for example, a frame-shift, or to the introduction of a additional amino acids into the Msi2 protein, or to the introduction of nucleic acid sequence not encoding amino acids, or the introduction of large inserts (e.g., T-DNA insertion), thereby impairing the provision/expression of functional Msi2 protein.

Impairment at the translational level can be achieved by the introduction of a premature stop codon or by influencing other RNA to protein processing mechanisms (such as splicing) or post-translational modification influencing, for example, protein folding or cellular trafficking.

Impairment or loss-of-function at the protein level can be provided by truncation, or by modification of amino acid residues important for activity, substrate binding, co-factor binding, folding, protein-protein interactions, and the like.

Impairment of expression of functional Msi2 protein may also be accomplished by gene silencing, for example, using CRISP, RNAi, VIGS, or the like.

Additionally, impairment of expression of functional Msi2 protein may be achieved by using Msi2 protein inhibitors such as an antibody specifically binding the Msi2 protein, or other Msi2 inhibitors, e.g. proteins that block, prevent or reduce the activity of endogenous Msi2 protein, or chemical inhibitors such as ions, or metals, or scavenging of co-factors. For example, an antibody specifically binding Msi2 protein may be expressed simultaneously with said Msi2 protein, thereby reducing its specific activity.

Msi2 Protein Comprising a Loss-of-Function Mutation

The present invention provides an Msi2 protein, preferably of plant origin, comprising one or more loss-of-function mutations. When a plant that expresses such Msi2 protein comprising one or more loss-of-function mutations and lacks expression of, or has suppressed expression of, endogenous Msi2 protein, is crossed to a wild type plant expressing endogenous Msi2 protein, haploid plants are formed at relatively high frequency. Haploid plants are formed at a more than normal frequency, such as at least 0.1, 0.5, 1, 5, 10, 20%, or more. Msi2 protein comprising one or more loss-of-function mutations can be created by a variety of means known to the skilled person. These include, without limitation, random mutagenesis, single or multiple amino acid targeted mutagenesis, generation of complete or partial protein domain deletions, fusion with heterologous amino acid sequences, and the like. Typically, the polynucleotide encoding endogenous Msi2 protein will be knocked out or inactivated to create a plant that lacks expression of endogenous Msi2 protein.

Msi2 protein comprising one or more loss-of-function mutations can, for example, be tested by recombinant expression of the Msi2 protein comprising one or more loss-of-function mutations in a plant lacking expression of endogenous Msi2 protein, crossing the transgenic plant to a plant expressing endogenous Msi2 protein, and then screening for the production of haploid progeny.

Any number of mutations can be introduced into an endogenous Msi2 protein to generate an Msi2 protein comprising one or more loss-of-function mutations. For example, the Msi2 protein comprising one or more loss-of-function mutations may be identical to the endogenous Msi2 protein but for 1, 2, 3, 4, 5, 6, 7, 8, or more amino acids.

The Msi2 protein is preferably a plant Msi2 protein. The plant may be any plant, but preferably belongs to the Solanaceae family, more preferably to the genus *Solanum*, even more preferably to the species *Solanum lycopersicum*.

In an embodiment, the one or more loss-of-function mutations are made in the endogenous Msi2 protein as represented by an amino acid sequence as shown in any of SEQ ID NOs: 1, 10, 2, or 3. Alternatively or additionally, the one or more loss-of-function mutations may be made in the endogenous Msi2 protein as represented by an amino acid sequence as shown in any of SEQ ID NOs: 1, 10, 2, or 3, or a variant thereof having at least 70%, 75%, 80%, 85%, 90%, 91%, 92%, 93%, 94%, 95%, 96%, 97%, 98%, 99% or more, such as 100%, amino acid sequence identity to the amino acid sequence of any of SEQ ID NOs: 1, 10, 2, or 3, preferably over the entire length. Amino acid sequence identity is determined by pairwise alignment using the Needleman and Wunsch algorithm and GAP default parameters as defined above.

The one or more loss-of-function mutations within the Msi2 protein comprising one or more loss-of-function mutations may be located throughout the protein. In an embodiment, a loss-of-function mutation is located in a WD40 repeat or in a CAF1C domain of the endogenous Msi2 protein as represented by an amino acid sequence as shown in any of SEQ ID NO: 1, 10, 2, or 3, or a variant thereof as taught herein.

The Msi2 protein taught herein may be encoded by a plant Msi2 protein-encoding polynucleotide having a loss-of-function mutation. The protein, when present in a plant in the absence of its endogenous Msi2 protein, allows generation of some haploid progeny, or progeny with aberrant ploidy, when said plant is crossed with a wild-type plant, without affecting viability of said plant.

The Msi2 protein taught herein may be derived from the a polypeptide comprising the amino acid sequence of SEQ ID NO:1 or 10, or a variant thereof having at least 70%, more preferably at least 80%, even more preferably at least 90%, yet even more preferably at least 95%, most preferably at least 98% or 99% sequence identity to the amino acid sequence of SEQ ID NO:1 or 10, said protein being encoded by a plant Msi2 protein-encoding polynucleotide having a loss-of-function mutation, which protein, when present in a plant in the absence of its endogenous Msi2 protein, allows generation of some haploid progeny, or progeny with aberrant ploidy, when said plant is crossed with a wild-type plant.

The Msi2 protein taught herein may be derived from a polypeptide comprising the amino acid sequence of SEQ ID NO:2 or 3, or a variant thereof having at least 70%, more preferably at least 80%, even more preferably at least 90%, yet even more preferably at least 95%, most preferably at least 98% or 99% sequence identity to the amino acid sequence of SEQ ID NO:2, said polypeptide being encoded by a plant Msi2 protein-encoding polynucleotide having a loss-of-function mutation, which polypeptide, when present in a plant in the absence of its endogenous Msi2 protein, allows generation of some haploid progeny, or progeny with aberrant ploidy, when said plant is crossed with a wild-type plant.

The Msi2 protein taught herein may be derived from the polypeptide comprising the amino acid sequence of SEQ ID NO:3 or a variant thereof having at least 70%, more preferably at least 80%, even more preferably at least 90%, yet even more preferably at least 95%, most preferably at least 98% or 99% sequence identity to the amino acid sequence of SEQ ID NO:3, said polypeptide being encoded by a plant Msi2 protein-encoding polynucleotide having loss-of-function mutation, which, when present in a plant in the absence of its endogenous Msi2 protein, allows generation of some haploid progeny, or progeny with aberrant ploidy, when said plant is crossed with a wild-type plant.

Suitably, at least 0.1, 0.5, 1 or 5% of the progeny produced when a plant as taught herein is crossed with a wild-type plant, is haploid, or has an aberrant ploidy, or is doubled-haploid.

In an embodiment, the one or more loss-of-function mutations introduce a premature stop codon that causes truncation of the protein.

In one embodiment, the protein is truncated after the amino acid residue at position 125 in SEQ ID NO:2 or 3.

In an embodiment, the Msi2 protein taught herein is encoded by a nucleic acid molecule comprising the nucleic acid sequence of SEQ ID NO:4 or 9.

Polynucleotides Encoding an Msi2 Protein Comprising One or More Loss-of-Function Mutations, Chimeric Genes, Vectors, Host Cells Polynucleotides having nucleic acid sequences, such as cDNA, genomic DNA and RNA molecules, encoding any of the above proteins are also provided. Due to the degeneracy of the genetic code a variety of nucleic acid sequences may encode the same amino acid sequence. Any polynucleotides encoding Msi2 proteins or variants thereof are herein referred to as "Msi2 protein-encoding polynucleotides". The polynucleotides provided include naturally occurring, artificial or synthetic nucleic acid sequences. It is understood that when sequences are depicted as DNA sequences while RNA is referred to, the actual base sequence of the RNA molecule is identical with the difference that thymine (T) is replace by uracil (U).

The present invention further relates to a polynucleotide encoding a Msi2 protein comprising one or more loss-of-function mutations as taught herein. Said polynucleotide may be a synthetic, recombinant and/or isolated polynucleotide. In an embodiment, said polynucleotide is derived from an endogenous Msi2 protein-encoding polynucleotide, e.g., an Msi2 gene, that comprises the nucleic acid sequence of SEQ ID NO:5, 7, or 8, or a variant thereof having at least 70%, preferably at least 75%, such as 80%, 85%, 90%, 95%, more preferably at least 97%, 98%, or 99% sequence identity to the nucleic acid sequence of SEQ ID NO: 5, 7, or 8, preferably over the full length, and which shares the endogenous Msi2 activity of the polypeptide comprising the amino acid sequence of SEQ ID NO:5, 7, or 8. In contrast, the Msi2 protein-encoding polynucleotide comprising one or more loss-of-function mutations taught herein comprises one or more mutations that reduce(s) or eliminate(s) endogenous Msi2 activity to less than 90, 80, 70, 60, 50, 40, 30, 20, 10% of Msi2 activity of endogenous Msi2 protein. Preferably, when present in a plant in the absence of the endogenous Msi2 protein-encoding polynucleotide, the Msi2 protein taught herein allows generation of some haploid progeny, or progeny with aberrant ploidy, when said plant is crossed with a wild-type plant.

The nucleic acid molecule as taught herein may be used for producing a haploid inducer line.

In one embodiment of the invention, nucleic acid sequences encoding Msi2 proteins (including Msi2 proteins comprising one or more loss-of-function mutations, or variants or fragments thereof), as described above, are used to make chimeric genes, and/or vectors for transfer of the Msi2 protein-encoding polynucleotides into a host cell and production of the Msi2 protein(s) in host cells, such as cells, tissues, organs or organisms derived from transformed cell (s). Vectors for the production of Msi2 protein (or protein fragments or variants thereof) as taught herein in plant cells are herein referred to as "expression vectors".

Suitable host cells for expression of Msi2 proteins include prokaryotes, yeast, or higher eukaryotic cells. Appropriate cloning and expression vectors for use with bacterial, fungal, yeast, and mammalian cellular hosts are described, for example, in Pouwels et al., Cloning vectors: A Laboratory Manual, Elsevier, N.Y., (1985). Cell-free translation systems could also be employed to produce the proteins of the present invention using RNAs derived from nucleic acid sequences disclosed herein.

Suitable prokaryotic host cells include gram-negative and gram-positive organisms, for example, *Escherichia coli* or *Bacilli*. Another suitable prokaryotic host cell is *Agrobacterium*, in particular *Agrobacterium tumefaciens*.

Msi2 proteins as taught herein can also be expressed in yeast host cells, for example from the *Saccharomyces* genus (e.g., *Saccharomyces cerevisiae*). Other yeast genera, such as *Pichia* or *Kluyveromyces*, can also be employed.

Alternatively, Msi2 proteins as taught herein may be expressed in higher eukaryotic host cells, including plant cells, fungal cells, insect cells, and mammalian, optionally non-human, cells.

One embodiment of the invention is a non-human organism modified to comprise a polynucleotide as taught herein. The non-human organism and/or host cell may be modified by any methods known in the art for gene transfer including, for example, the use of delivery devices such as lipids and viral vectors, naked DNA, electroporation, chemical methods and particle-mediated gene transfer. In an advantageous embodiment, the non-human organism is a plant.

Any plant cell may be a suitable host cell. The term "plant cell" as used herein includes protoplasts. Suitable plant cells include those from monocotyledonous plants or dicotyledonous plants. For example, the plant may belong to the genus *Solanum* (including *Lycopersicon*), *Nicotiana*, *Capsicum*, *Petunia* and other genera. The following host species may suitably be used: Tobacco (*Nicotiana* species, e.g. *N. benthamiana*, *N. plumbaginifolia*, *N. tabacum*, etc.), vegetable species, such as tomato (*L. esculentum*, syn. *Solanum*

*lycopersicum*) such as e.g. cherry tomato, var. cerasiforme or currant tomato, var. *pimpinellifolium*) or tree tomato (*S. betaceum*, syn. *Cyphomandra betaceae*), potato (*Solanum tuberosum*), eggplant (*Solanum melongena*), pepino (*Solanum muricatum*), cocona (*Solanum sessiliflorum*) and naranjilla (*Solanum quitoense*), peppers (*Capsicum annuum, Capsicum frutescens, Capsicum baccatum*), ornamental species (e.g. *Petunia hybrida, Petunia axillaries, P. integrifolia*), coffee (*Coffea*).

Alternatively, the plant may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (Oryza species, e.g. *O. sativa* indica cultivar-group or japonica cultivar-group), forage grasses, pearl millet (*Pennisetum* spp. e.g. *P. glaucum*), tree species (Pinus, poplar, fir, plantain, etc), tea, *coffea*, oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. *Rose, Petunia, Chrysanthemum, Lily, Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana*.

Preferred host cells are derived from "crop plants" or "cultivated plants", i.e. plant species which is cultivated and bred by humans. A crop plant may be cultivated for food or feed purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork, fibres (such as cotton) and the like.

The construction of chimeric genes and vectors for, preferably stable, introduction of Msi2 protein-encoding nucleic acid sequences as taught herein into the genome of host cells is generally known in the art. To generate a chimeric gene the nucleic acid sequence encoding a Msi2 protein as taught herein is operably linked to a promoter sequence, suitable for expression in the host cells, using standard molecular biology techniques. The promoter sequence may already be present in a vector so that the Msi2 protein-encoding nucleic acid sequence is simply inserted into the vector downstream of the promoter sequence. The vector may then be used to transform the host cells and the chimeric gene may be inserted in the nuclear genome or into the plastid, mitochondrial or chloroplast genome and expressed using a suitable promoter (e. g., Mc Bride et al., 1995 Bio/Technology 13, 362; U.S. Pat. No. 5,693,507). In an embodiment the chimeric gene as taught herein comprises a suitable promoter for expression in plant cells or microbial cells (e.g. bacteria), operably linked to a nucleic acid sequence encoding a Msi2 protein as taught herein, optionally followed by a 3'nontranslated nucleic acid sequence. The bacteria may subsequently be used for plant transformation (*Agrobacterium*-mediated plant transformation).

The present invention also relates to plants, particularly crop plants, more particularly plants belonging to the family Solanaceae, more particularly to the genus *Solanum*, yet more particularly to the species *Solanum lycopersicum*, which lack expression of functional Msi2 protein, either due to: 1) prevention or reduction of expression of the Msi2 gene, e.g., by knocking out the Msi2 gene; 2) prevention or reduction of translation of mRNA transcribed from the Msi2 gene; or 3) the expression of a non-functional Msi2 protein.

Plants Expressing Msi2 Polypeptides Comprising One or More Loss-of-Function Mutations The present invention provides plants, seeds, or plant cells expressing a Msi2 polypeptide comprising one or more loss-of-function mutations as taught herein. The present invention also provides plants, seed, or plant cells comprising a polynucleotide as taught herein, a chimeric gene as taught herein, or a vector as taught herein. The plant, seed, or plant cell preferably belongs to the family Solanaceae, more preferably to the genus *Solanum*, yet more preferably to the species *Solanum lycopersicum*.

The plants, seeds, or plant cells preferably do not express, or express at reduced levels (e.g., less than 90, 80, 70, 60, 50, 40, 30, 20, 10% of wild type levels), an endogenous Msi2 protein. For example, one can generate a mutation in an endogenous Msi2 protein that reduces or eliminates endogenous Msi2 protein activity or expression, or one can generate a knockout for endogenous Msi2 protein. In this case, one may generate a plant heterozygous for the gene knockout or mutation and introduce an expression vector for expression of a Msi2 protein comprising one or more loss-of-function mutations as taught herein in the plant. Progeny from the heterozygote can then be selected that are homozygous for the mutation or knockout but that comprise the Msi2 protein comprising one or more loss-of-function mutations.

Accordingly, in plants, seeds, or plant cells taught herein preferably one or both endogenous Msi2 alleles are knocked out or mutated such that said plants or plant cells significantly or essentially completely lack endogenous Msi2 activity. It was found that such plants are viable. In plants having more than a diploid set of chromosomes, all endogenous Msi2 alleles may be inactivated, mutated or knocked out. Alternatively, the expression of endogenous Msi2 protein may be silenced by any way known in the art, e.g. by introducing a siRNA or microRNA that reduces or eliminates expression of endogenous Msi2 protein.

In an embodiment, the invention pertains to a *Solanum lycopersicum* plant, seed, or plant cell comprising the nucleic acid molecule as taught herein.

In an embodiment, the invention pertains to a *Solanum lycopersicum* plant, seed, or plant cell comprising a nucleic acid molecule that encodes a Msi2 protein as taught herein.

In an embodiment, said *Solanum lycopersicum* plant, seed, or plant cell comprises a nucleic acid molecule encoding a polypeptide comprising the amino acid sequence of SEQ ID NO:6.

In an embodiment, said *Solanum lycopersicum* plant, seed, or plant cell comprises the nucleic acid molecule of SEQ ID NO:4 or 9.

Said *Solanum lycopersicum* plant, seed, or plant cell may be used for producing a haploid *Solanum lycopersicum* plant, and/or for producing a doubled haploid *Solanum lycopersicum* plant.

In an embodiment, said *Solanum lycopersicum* plant, seed, or plant cell lacks expression of endogenous Msi2 protein at least during embryonic development.

Methods for the Generation of Plants

It is an embodiment of the invention to modify an endogenous Msi2 gene using targeted mutagenesis methods (also referred to as targeted nucleotide exchange (TNE) or oligo-directed mutagenesis (ODM)). Targeted mutagenesis methods include, without limitation, those employing zinc finger nucleases, Cas9-like, Cas9/crRNA/tracrRNA or Cas9/gRNA CRISPR systems, or targeted mutagenesis methods employing mutagenic oligonucleotides, possibly containing chemically modified nucleotides for enhancing mutagenesis with sequence complementarity to the Msi2 gene, into plant protoplasts (e.g., KeyBase® or TALENs).

Alternatively, mutagenesis systems such as TILLING (Targeting Induced Local Lesions IN Genomics; McCallum et al., 2000, Nat Biotech 18:455, and McCallum et al. 2000, Plant Physiol. 123, 439-442, both incorporated herein by reference) may be used to generate plant lines which comprise a Msi2 gene encoding a Msi2 protein comprising one or more loss-of-function mutations. TILLING uses traditional chemical mutagenesis (e.g. EMS mutagenesis) followed by high-throughput screening for mutations. Thus, plants, seeds and tissues comprising a Msi2 gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Modified plants may be distinguished from non-modified plants, i.e., wild type plants, by molecular methods, such as the mutation(s) present in the DNA, and by the modified phenotypic characteristics. The modified plants may be homozygous or heterozygous for the mutation.

Thus, a method for making a plant as taught herein is provided, said method comprising the steps of:
a) modifying a nucleic acid molecule encoding an endogenous Msi2 protein within a plant cell to obtain a mutated nucleic acid molecule encoding an Msi2 protein as taught herein, or modifying a nucleic acid molecule encoding an endogenous Msi2 protein within a plant cell in order to prevent expression of, or knock out expression of, said endogenous Msi2 protein within a plant cell;
b) selecting a plant cell comprising the mutated nucleic acid molecule, or a plant cell in which expression of said endogenous Msi2 protein is prevented or knocked out; and
c) optionally, regenerating a plant from said plant cell.

The invention further provides a method for making a plant as taught herein comprising the steps of:
a) transforming a plant cell with a nucleic acid molecule as taught herein, a chimeric gene as taught herein, or a vector as taught herein, or transforming a plant cell with a nucleic acid molecule in order to prevent expression of, or knock out expression of, an endogenous Msi2 protein;
b) optionally, additionally modifying in said plant cell a nucleic acid molecule encoding an endogenous Msi2 protein in order to prevent expression of, or knock out expression of, an endogenous Msi2 protein;
c) selecting a plant cell comprising the nucleic acid molecule as taught herein, a chimeric gene as taught herein, or a vector as taught herein, or a plant cell in which expression of endogenous Msi2 protein is prevented or knocked out; and
d) optionally, regenerating a plant from said plant cell.

The present invention also provides a method for making a plant as taught herein, comprising the steps of: i) transforming a plant cell with a polynucleotide as taught herein, a chimeric gene as taught herein, or a vector as taught herein;
ii) selecting a plant cell comprising said polynucleotide; and
iii) optionally, regenerating a plant from said plant cell.

The methods for making a plant as taught herein may further comprise the step of modifying an endogenous plant Msi2 protein-encoding polynucleotide within said plant cell to prevent expression of endogenous Msi2 protein.

The Msi2 protein-encoding polynucleotides, preferably a Msi2 protein-encoding chimeric gene, as taught herein can be stably inserted in a conventional manner into the nuclear genome of a single plant cell, and the so-transformed plant cell can be used in a conventional manner to produce a transformed plant that has an altered phenotype due to the presence of the Msi2 protein as taught herein in certain cells at a certain time. In this regard, a T-DNA vector, comprising a Msi2 protein-encoding polynucleotide as taught herein, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO84/02913 and published European Patent application EP 0 242 246 and in Gould et al. (1991, Plant Physiol. 95,426-434). The construction of a T-DNA vector for *Agrobacterium* mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718.

Likewise, selection and regeneration of transformed plants from transformed plant cells is well known in the art. Obviously, for different species and even for different varieties or cultivars of a single species, protocols are specifically adapted for regenerating transformants at high frequency.

The resulting transformed plant can be used in a conventional plant breeding scheme to produce haploid plants that may subsequently become doubled haploid plants.

Methods for the Generation of Haploid Plants and/or Doubled Haploid Plants

The invention also relates to a method of generating a haploid plant, a plant with aberrant ploidy, or a doubled haploid plant, said method comprising the steps of:
a) crossing a plant expressing an endogenous Msi2 protein to the modified plant as taught herein, wherein the modified plant as taught herein lacks expression of endogenous Msi2 protein at least during embryonic development;
b) harvesting seed;
c) growing at least one seedling, plantlet or plant from said seed; and d) selecting a haploid seedling, plantlet or plant, a seedling, plantlet or plant with aberrant ploidy, or a doubled haploid seedling, plantlet or plant.

Said plant expressing an endogenous Msi2 protein may be an F1 plant.

The plant expressing the endogenous Msi2 protein may be a pollen parent of the cross, or may be an ovule parent of the cross.

Crossing a modified plant as taught herein, lacking expression of endogenous Msi2 protein, to a wild-type plant will result in at least some progeny that is haploid and comprises only chromosomes from the plant that expresses the endogenous Msi2 protein. Thus, the present invention allows for the generation of haploid plants having all of its chromosomes from a plant of interest by crossing the plant of interest with a plant lacking expression of functional Msi2 protein, and collecting the resulting haploid seed.

Thus, genome elimination can be engineered with a precise molecular change independent of parental genotype. Msi2 protein is found in any plant species. This allows haploid plants to be made in species where conventional methods for haploid plant production, such as tissue culture of haploid cells and wide crosses, are unsuccessful.

The plant lacking expression of functional Msi2 protein as taught herein may be crossed as either the male or female parent. The methods taught herein allow for transfer of paternal chromosomes into maternal cytoplasm. Thus, it can generate cytoplasmic male sterile lines with a desired genotype in a single step.

The invention further relates to a method of generating a doubled haploid plant, said method comprising the steps of:

a) crossing a plant expressing an endogenous Msi2 protein to the modified plant as taught herein, wherein the modified plant as taught herein lacks expression of endogenous Msi2 protein at least during embryonic development;

b) selecting a haploid plant; and c) converting said haploid plant into a doubled haploid plant.

Thus, once generated, haploid plants can be used for the generation of doubled haploid plants, which comprise an exact duplicate copy of chromosomes. A wide variety of methods are known for generating doubled haploid organisms from haploid organisms. For example, chemicals such as colchicine may be applied to convert the haploid plant into a doubled haploid plant. Alternatively, ploidy may double spontaneously during embryonal development or at a later developmental stage of a plant.

Doubled haploid plants can be further crossed to other plants to generate F1, F2, or subsequent generations of plants with desired traits.

Doubled haploids plants may be obtained that do not bear transgenic or mutagenized genes. Additionally, doubled haploid plants can rapidly create homozygous F2s from a hybrid F1.

The invention also relates to a method of generating a haploid or doubled haploid plant, said method comprising the step of identifying a plant expressing an endogenous Msi2 protein and a plant as taught herein, wherein the plant as taught herein lacks expression of endogenous Msi2 protein at least in its reproductive parts and/or during embryonic development.

In an embodiment, crossing does not comprise sexually crossing the whole genomes of plants. Instead, one set chromosomes is eliminated.

BRIEF DESCRIPTION OF THE FIGURE

FIG. 1 shows a tetrad of a Msi2-K126-stop mutant. The arrow shows a micronucleus.

SEQUENCE LISTING

SEQ ID NO:1: plant Msi2 consensus protein sequence
SEQ ID NO:2: *Solanum consensus* Msi2 protein sequence
SEQ ID NO:3: *Solanum lycopersicum* Msi2 protein sequence
SEQ ID NO:4: *Solanum lycopersicum* Msi2_K126* coding sequence
SEQ ID NO:5: *Solanum lycopersicum* Msi2 coding sequence
SEQ ID NO:6: *Solanum lycopersicum* Msi2_K126* truncated protein sequence
SEQ ID NO:7: *Solanum consensus* Msi2 coding sequence
SEQ ID NO:8—*Solanum lycopersicum* Msi2 genomic DNA sequence
SEQ ID NO:9—*Solanum lycopersicum* Msi2_K126* genomic DNA sequence
SEQ ID NO:10—*Solanaceae consensus* Msi2 protein sequence

EXAMPLES

Example 1: Uniparental Genome Elimination in Tomato

Material and Methods

Plant Material

Three tomato cultivars were used namely "MoneyBerg TMV+", "MicroTom" and "RZ52201". From a tomato RZ52201 mutant population, following methods described in WO 2007/037678 and WO2009/041810, two somatic non-synonymous mutants in the gene Msi2 were selected, namely Msi2_K126-STOP and Msi2_K126M, which are both mutated at amino acid position 126. The selected mutant plant was self-pollinated and in the offspring, plants were selected that were homozygous for the mutated locus. From a tomato MoneyBerg TMV+ mutant population a somatic synonymous mutant was selected, following methods described in WO 2007/037678 and WO2009/041810, in the gene Msi2, namely Msi2_D337D, which is mutated at amino acid position 337 (C to T). The selected mutant plant was self-pollinated and in the offspring, plants were selected that were homozygous for the mutated locus.

Method

Uni-parental genome elimination and the resulting production of a haploid plant was provoked by making a cross between a so called haploid inducer line and another non-haploid inducer line, for example a breeding line. Crosses of tomato lines for uni-parental genome elimination were performed at relatively high temperatures (26-28° C.), since it is known that an elevated temperature can, but only in some cases, have a positive effect on the occurrence of uni-parental genome elimination (Sanei et al. PNAS 108.33 (2011): E498-E505).

Results

The non-synonymous mutation of A to T in the Msi2_K126-STOP mutant resulted in the introduction of a premature stop codon and thereby the production of a truncated protein (SEQ ID NO:6). The non-synonymous mutation of A to T in the Msi2_K126M mutant resulted in an amino acid modification of a lysine to a methionine. Furthermore a SIFT analysis was run for the Msi2 protein and the mutation of a lysine to a methionine at position 126 was rated by this analysis to be neutral (Kumar et al. Nat Protoc. 2009; 4(7):1073-81). The synonymous mutation of C to T in the Msi2_D337D mutant did not result in an amino acid modification. Each of the three mutant plants homozygous for the Msi2_K126-STOP, the Msi2_K126M or the Msi2_D337D mutation were used as pollen donor and as female in crosses at relatively high temperatures (26-28° C.) using non-mutated wild type MicroTom plants as female or pollen donor, respectively. Table 1 lists an overview of all crosses made and the sown seeds which were evaluated for the MicroTom phenotype.

TABLE 1

List of crosses made; genetic background of the parents used, number of offspring plants tested and number of offspring plants which showed MicroTom dwarf phenotype.

| Plant used as female | Plant used as male | Background mutant parent | Number of plants tested | Number of plants with MicroTom phenotype | Year |
|---|---|---|---|---|---|
| Msi2_K126-STOP | MicroTom | RZ52201 | 98 | 3 | 2014 |
| MicroTom | Msi2_K126-STOP | RZ52201 | 89 | 2 | 2014 |
| Msi2_K126-STOP | MicroTom | RZ52201 | 564 | 4 | 2015 |
| MicroTom | Msi2_K126-STOP | RZ52201 | 325 | 1 | 2015 |
| Msi2_K126M | MicroTom | RZ52201 | 19 | 0 | 2014 |
| MicroTom | Msi2_K126M | RZ52201 | 205 | 0 | 2014 |
| Msi2_D337D | MicroTom | MoneyBergTMV+ | 160 | 0 | 2014 |
| MicroTom | Msi2_D337D | MoneyBergTMV+ | 36 | 0 | 2014 |
| RZ52201 | MicroTom | — | 188 | 0 | 2015 |
| MicroTom | RZ52201 | — | 188 | 0 | 2015 |

Seeds derived from the crosses listed in table 1 were sown and the plants were evaluated for their DNA content by means of flow cytometry. The flow cytometry analysis resulted in a determination of only normal diploid ploidy levels for all plants tested, similar to wild type tomato cultivars such as MoneyBergTMV+. The cultivar MicroTom has a dwarf phenotype, which is known to be recessive (Marti et al, J Exp Bot, Vol. 57, No. 9, pp. 2037-2047, 2006). After a cross of MicroTom to or with, for instance a MoneyBerg TMV+ or RZ52201 wild type cultivar, one only finds offspring with the indeterminate non-dwarf phenotype of the MoneyBerg TMV+ or RZ52201 wild type cultivar, respectively. The same was found for crosses with the Msi2_D337D synonymous mutant and MicroTom; all offspring of a MicroTom and Msi2_D337D mutant crosses showed the indeterminate non-dwarf phenotype of the MoneyBerg TMV+ parent. Reciprocal crosses of MicroTom and the Msi2_K126M mutant did not result in offspring with the MicroTom phenotype. Using the Msi2_K126-STOP mutant as male or female parent, in total 10 plants were found which showed a MicroTom phenotype. This indicates that the RZ52201 parent genetic material is not part of the resulting offspring and this indicates that these 10 offspring plants are of haploid MicroTom origin. The ploidy of all plants of the latter 10 plants was found to be diploid, indicating that spontaneous doubling had occurred, a phenomena which has been described to have an exceptional high frequency of appearance for tomato (Report of the Tomato Genetics Cooperative Number 62-December 2012).

In order to determine whether and to what extent uniparental genome elimination had occurred, a single nucleotide polymorphism (SNP) assay was run for in total 44 positions for the 2014 offspring, spread across each of the 12 tomato chromosomes (4 SNPs on chromosome 1, 2, 3, 4, 5, 6, 11 and 12; 3 SNPs on chromosome 8 and 10; 2 SNPs on chromosome 9). The same analysis was performed for the 2015 offspring, now on 22 positions (2 SNPs on chromosome 1, 2, 3, 4, 5, 6, 7, 8, 10 and 12; 1 SNP on chromosome 9 and 11). The single 5 nucleotide polymorphisms selected were homozygous for one base pair for the MicroTom parent and homozygous for all but not the MicroTom base pair in the RZ52201 parent. A regular cross between a wild type MicroTom cultivar and the RZ52201 cultivar would result in a heterozygous single nucleotide polymorphism score. However, when the process of uniparental genome elimination has occurred, one expects the loss of the haploid inducer line genome. The single nucleotide polymorphism test resulted in calling of only homozygous base pair scores from the MicroTom parent for each of the 5 offspring plants which also showed the MicroTom phenotype and none of the RZ52201 parent were called. Based on the single nucleotide polymorphism scores it was concluded that the complete genome of the Msi2_K126-STOP mutant was no longer present in the offspring. Therefore, it can be concluded that the Msi2_K126-STOP mutant functions as a highly efficient haploid inducer line. In the crosses in which the Msi2_K126-STOP mutant was used as female parent, a selfing of MicroTom can be ruled out. It is highly unlikely that in the experiment using MicroTom as female parent selfing took place, given the very low number of offspring showing the MicroTom phenotype (only 2 seeds out of 89 and 1 seed out of 325), and the fact that only homozygous base pairs were scored.

Pollen tetrads of the Msi2-K126-stop mutant and of RZ52201 control plants were checked for occurrence of aberrancies. From four different flower trusses at least two flowers were taken and anthers were squashed in order to look at pollen tetrads. For the Msi2-K126-stop mutant, in all 10 observed anthers from 5 individual flowers, micronuclei were observed (see FIG. 1). In each observed anther several examples of micronuclei were found, however not more than 1% of the pollen tetrads in an anther showed the aberrancies. For the RZ52201 control, rarely an anther was observed containing pollen tetrads with micronuclei. Two anthers were found in which in total only two or three examples of micronuclei could be observed. In a second round of experiments, the micronuclei were counted; For the Msi2-K126-stop mutant, micronuclei were observed with a frequency of 1.94% (n=1). For the RZ52201 control plant flowers, micronuclei were observed with an average frequency of 0.58±0.36% (n=5). It is concluded that the separation of chromosomes during meiosis is considerably more frequently disturbed as a result on the Msi2-K126-stop mutation compared to the control. Aberrant mitosis, for instance observations of micronuclei, are often used as direct evidences of chromosome elimination and haploid production in inter-, intra-specific hybridizations in crops. For example, aberrant mitosis as well as aberrant meiosis, for instance micronuclei, were found in a study of a maize DH-inducer line (Qiu, Fazhan, et al. Current Plant Biology 1 (2014): 83-90). The observations of meiosis micronuclei in the Msi2-K126-stop mutant, suggest that during mitosis similar processes occur. It is likely that the process of uniparental genome elimination during the first mitotic divisions after fusion of wild type and Msi2-K126-stop zygotes takes place and that this results in the observed induction of haploids.

Example 2: Uniparental Genome Elimination in Arabidopsis

Materials and Methods

Plant Material

The following Arabidopsis NASC stock centre accessions were used; Columbia (background line, Col-0, N1092), Col-5 (N1644), Arabidopsis Msi2 gene (At2g16780) T-DNA insertion lines (N720344 and N501214, in Col-0 background) and, since it is not known whether the Msi2 and Msi3 gene are functionally redundant genes, Arabidopsis Msi3 gene (At4g35050) T-DNA insertion mutants (N309860, N309863 and N564092 in Col-0 background). The T-DNA insertion lines were evaluated by means of PCR amplification and subsequent sequencing of the putative T-DNA insertion locus in order to determine the exact insertion in the Arabidopsis Msi2 and Msi3 genes. Based on the finding that the insertions were located in exons of either Msi2 or Msi3 genes it was concluded that these T-DNA insertion lines are true knock-outs for either the Msi2 or Msi3 gene. The exact positions as counted in number of bases downstream of the start codon were; N720344 (position 429, exon 2), N501214 (position 111, exon 1), N309863/N309860 (both in position 559, exon 2) and N564092 (position 1237, exon 6). By making crosses between two insertion lines and selecting for homozygous T-DNA insertions in both the Msi2 and the Msi3 gene, two novel double T-DNA insertion lines were produced; N720344+N309860 and N309863+N501214.

Method

Uni-parental genome elimination and the resulting production of a haploid plant is provoked by making a cross between a so called haploid inducer line and another non-haploid inducer line, for example a Columbia background (Col-0) control line.

Results

Either a single T-DNA insertion line for Msi2 (N720344 and N501214), a Msi3 T-DNA insertion line (N309863 and N564092), the two newly generated Msi2/Msi3 double T-DNA insertion lines (N720344+N309860 and N309863+N501214) or Col-0 background plants are used as pollen donor and as female in crosses using Col-5 as female or pollen donor, respectively. Table 2 lists an example of typical crosses which can be made and an example of the evaluation of the offspring for the Col-5 phenotype. Col-5 has a clear distinct recessive phenotype compared to the T-DNA insertion lines and Col-0, namely trichomeless leaves.

TABLE 2

List of crosses which can be made; genetic background of all insertion lines was Col-0, and number of offspring plants which are tested.

| Plant used as female | Plant used as male | Number of plants tested |
| --- | --- | --- |
| Msi2 (N720344) | Col-5 | 300 |
| Col-5 | Msi2 (N720344) | 300 |
| Msi2 (N501214) | Col-5 | 300 |
| Col-5 | Msi2 (N501214) | 300 |
| Msi3 (N309863) | Col-5 | 300 |
| Col-5 | Msi3 (N309863) | 300 |
| Msi3 (N564092) | Col-5 | 300 |
| Col-5 | Msi3 (N564092) | 300 |
| Msi2/Msi3 (N720344 + N309860) | Col-5 | 300 |
| Col-5 | Msi2/Msi3 (N720344 + N309860) | 300 |
| Msi2/Msi3 (N309863 + N501214) | Col-5 | 300 |
| Col-5 | Msi2/Msi3 (N309863 + N501214) | 300 |
| Col-0 | Col-5 | 300 |
| Col-5 | Col-0 | 300 |

The Col-5 accession harbours the gl1-1/gl1-1 locus giving it a trichomeless phenotype, which is known to be recessive (Kuppu et al. PLoS Genet 11.9 2015 e1005494). After a cross of Col-5 to or with, for instance a Col-0 wild type cultivar, one only finds offspring with trichomes coming from the dominant Col-0 allele. Using Msi2 single, Msi3 single or Msi2/Msi3 double T-DNA insertion lines as male or female parent, in total several plants are found which show a trichomeless phenotype. This indicates that the Col-0 parent genetic material is not part of the resulting offspring and this indicates that these offspring plants are of haploid Col-5 origin.

Based on the single Col-5 phenotype individuals among the offspring of the crosses performed, it is concluded that the complete genome of the respective T-DNA insertion line in the Col-0 background is no longer present in the offspring. Therefore, it is concluded that the T-DNA insertion lines "N720344, N501214, N309863, N564092, N720344+ N309860 (double insertion line) and N309863+N501214 (double insertion line) function as highly efficient (doubled) haploid inducer lines.

The invention claimed is:

1. A Msi2 gene comprising a loss-of-expression mutation, wherein the Msi2 gene is derived from a gene encoding an Msi2 protein having at least 70% sequence identity with at least one of SEQ ID NO. 1, 2, 3 and 10,
wherein the loss-of-expression mutation results in reduced expression of the Msi2 protein,
wherein the gene is not an *Arabidopsis thaliana*-derived Msi2 gene, and
wherein the Msi2 gene, when present in a plant in the absence of the endogenous Msi2 gene, allows generation of haploid progeny, or progeny with aberrant ploidy, at a more than normal frequency when the plant is crossed with a wild-type plant.

2. The gene according to claim 1, wherein the sequence encoding the Msi2 protein has at least 90% sequence identity with at least one of SEQ ID NO: 5 and 7.

3. The gene according to claim 1, wherein the expression of the Msi2 protein is knocked out.

4. The gene according to claim 1, wherein the loss-of-expression mutation is in a transcription regulation sequence.

5. The gene according to claim 1, wherein the mutation is at least one of a frame-shift mutation, deletion, substitution, rearrangement or insertion of nucleotides in the Msi2-coding region.

6. The gene according to claim 1, herein at least 10% of the Msi2-coding region is removed.

7. A plant, seed, or plant cell comprising the Msi2 gene of claim 1.

8. The plant, seed or plant cell according to claim 7, wherein the expression of an endogenous Msi2 protein is reduced or knocked out.

9. The plant, seed or plant cell according to claim 7, which is a *Solanum* plant, seed or plant cell.

10. The plant, seed or plant cell according to claim 8, wherein the *Solanum* plant, seed or plant cell is a *Solanum lycopersicum*.

11. A method for producing a plant, seed, or plant cell, the method comprising:
(a) modifying an endogenous Msi2 gene within a plant cell to obtain the mutated Msi2 gene, wherein the gene comprises a loss-of-expression mutation resulting in a reduced expression of the Msi2 protein, and wherein the gene is not an *Arabidopsis thaliana*-derived Msi2 gene;
(b) selecting a plant cell comprising the mutated Msi2 gene; and
(c) optionally, regenerating a plant from said plant cell.

12. A method of generating a haploid plant, a plant with aberrant ploidy, or a doubled haploid plant, comprising:
(a) crossing a plant expressing an endogenous Msi2 protein with a plant of claim 7 wherein the plant lacks expression of endogenous Msi2 protein at least in its reproductive parts and/or during embryonic development;
(b) harvesting seed;
(c) growing at least one seedling, plantlet or plant from said seed; and
(d) selecting a haploid seedling, plantlet or plant, a seedling, plantlet or plant with aberrant ploidy, or a doubled haploid seedling, plantlet or plant.

13. A method of generating a doubled haploid plant, comprising:
(a) crossing a plant expressing an endogenous Msi2 protein to the plant of claim 7, wherein the plant lacks expression of endogenous Msi2 protein at least in its reproductive parts and/or during embryonic development;
(b) selecting a haploid plant; and
(c) converting said haploid plant into a doubled haploid plant.

14. The method according to claim 13, wherein the conversion in (c) is performed by treatment with colchicine.

* * * * *

SEQUENCE LISTING

<160> NUMBER OF SEQ ID NOS: 10

<210> SEQ ID NO 1
<211> LENGTH: 396
<212> TYPE: PRT
<213> ORGANISM: Artificial Sequence
<220> FEATURE:
<223> OTHER INFORMATION: Description of Artificial Sequence: Synthetic
      plant Msi2 consensus protein sequence
<220> FEATURE:
<221> NAME/KEY: MOD_RES
<222> LOCATION: (7)..(7)
<223> OTHER INFORMATION: Any naturally occurring amino acid
<220> FEATURE:
<221> NAME/KEY: MOD_RES
<222> LOCATION: (12)..(12)
<223> OTHER INFORMATION: Any naturally occurring amino acid
<220> FEATURE:
<221> NAME/KEY: MOD_RES
<222> LOCATION: (27)..(27)
<223> OTHER INFORMATION: Any naturally occurring amino acid
<220> FEATURE:
<221> NAME/KEY: MOD_RES
<222> LOCATION: (91)..(91)
<223> OTHER INFORMATION: Any naturally occurring amino acid
<220> FEATURE:
<221> NAME/KEY: MOD_RES
<222> LOCATION: (153)..(153)
<223> OTHER INFORMATION: Any naturally occurring amino acid
<220> FEATURE:
<221> NAME/KEY: MOD_RES
<222> LOCATION: (193)..(193)
<223> OTHER INFORMATION: Any naturally occurring amino acid
<220> FEATURE:
<221> NAME/KEY: MOD_RES
<222> LOCATION: (256)..(256)
<223> OTHER INFORMATION: Any naturally occurring amino acid
<220> FEATURE:
<221> NAME/KEY: MOD_RES
<222> LOCATION: (362)..(362)
<223> OTHER INFORMATION: Any naturally occurring amino acid
<220> FEATURE:
<221> NAME/KEY: MOD_RES
<222> LOCATION: (396)..(396)
<223> OTHER INFORMATION: Any naturally occurring amino acid

<400> SEQUENCE: 1

Met Ala Glu Glu Gly Gly Xaa Glu Thr Gly Met Xaa Gln Val Glu Glu
1               5                   10                  15

Glu Phe Ser Val Trp Lys Lys Asn Thr Pro Xaa Leu Tyr Asp Leu Val
                20                  25                  30

Ile Ser His Pro Leu Glu Trp Pro Ser Leu Thr Val Gln Trp Leu Pro
            35                  40                  45

Ser Pro Ser Thr Asp Pro Ser Ala Phe Arg Val His Lys Leu Val Leu
        50                  55                  60

Gly Thr His Thr Ser Asp Glu Ala Pro Asn Phe Leu Met Val Ala Asp
65                  70                  75                  80

Ala Val Leu Pro Pro Arg Ala Ala Xaa Leu Ala Ala Gly Gly
                85                  90                  95

Ala Val Pro Ile Pro Lys Val Glu Ile Ser Gln Lys Ile His Val Asp
                100                 105                 110

Gly Glu Val Asn Arg Ala Arg Cys Met Pro Gln Arg Pro Tyr Thr Val
            115                 120                 125

Ala Ala Lys Thr Cys Gly Asp Glu Val His Val Phe Asp Leu Gly Lys
        130                 135                 140

Gly Gln Gly Ser Cys Gly Pro Asp Xaa Arg Leu Arg Gly His Asp Lys
145                 150                 155                 160

-continued

```
Glu Gly Tyr Gly Leu Ser Trp Ser Pro Phe Lys Glu Gly Tyr Leu Leu
            165                 170                 175

Ser Gly Ser Tyr Asp Lys Lys Ile Cys Leu Trp Asp Val Ser Ala Gly
            180                 185                 190

Xaa Gln Asp Lys Val Leu Asp Ala Met His Val Tyr Glu Ala His Glu
            195                 200                 205

Asp Val Val Glu Asp Val Ala Trp His Leu Lys Asn Glu Asn Leu Phe
            210                 215                 220

Gly Ser Val Gly Asp Asp Cys Lys Leu Met Ile Trp Asp Leu Arg Thr
225                 230                 235                 240

Asn Lys Pro Gln Gln Ser Val Lys Ala His Glu Lys Glu Val Asn Xaa
            245                 250                 255

Leu Ser Phe Asn Pro Phe Asn Glu Trp Ile Leu Ala Thr Ala Ser Ser
            260                 265                 270

Asp Ser Thr Val Lys Leu Phe Asp Leu Arg Lys Leu Ser Arg Pro Leu
            275                 280                 285

His Val Phe Ser Ser His Glu Gly Glu Val Phe Gln Val Glu Trp Asp
            290                 295                 300

Pro Asn His Glu Thr Val Leu Ala Ser Ser Ala Ala Asp Arg Arg Leu
305                 310                 315                 320

Met Val Trp Asp Leu Asn Arg Ile Gly Asp Glu Gln Leu Glu Glu Asp
            325                 330                 335

Ala Glu Asp Gly Pro Pro Glu Leu Leu Phe Ser His Gly Gly His Lys
            340                 345                 350

Ala Lys Ile Ser Asp Phe Ser Trp Asn Xaa Asn Glu Pro Trp Val Ile
            355                 360                 365

Ala Ser Val Ala Glu Asp Asn Ile Leu Gln Val Trp Gln Met Ala Glu
            370                 375                 380

Ser Ile Tyr Arg Asp Asp Asp Asn Ala Asp Xaa
385                 390                 395

<210> SEQ ID NO 2
<211> LENGTH: 403
<212> TYPE: PRT
<213> ORGANISM: Artificial Sequence
<220> FEATURE:
<223> OTHER INFORMATION: Description of Artificial Sequence: Synthetic
      Solanum consensus Msi2 protein sequence

<400> SEQUENCE: 2

Met Ala Glu Glu Glu Leu Glu Ala Ala Gly Glu Thr Glu Gln Asp Val
1               5                   10                  15

Glu Glu Glu Phe Ala Val Trp Lys Lys Asn Thr Pro Leu Leu Tyr Asp
            20                  25                  30

Leu Val Val Cys His Ala Leu Glu Trp Pro Ser Leu Thr Val Gln Trp
        35                  40                  45

Leu Pro Ser Pro Thr Thr Asp Asp Gly Ala Phe Ala Val His Lys Leu
    50                  55                  60

Ile Leu Gly Thr His Thr Ser Asp Asp Cys Pro Asn Phe Leu Met Val
65                  70                  75                  80

Ala Lys Val His Leu Pro Arg Asn Pro Ala Ser Gly Leu Glu His Asn
                85                  90                  95

Leu Met Asn Pro Gln Ile Pro Lys Val Glu Ile Val Gln Lys Ile His
            100                 105                 110

Val Asp Gly Glu Val Asn Arg Ala Arg Cys Met Pro Gln Lys Pro Ala
        115                 120                 125
```

```
Val Val Ala Ala Lys Thr Ser Ser Glu Val Tyr Val Phe Asp Ser
    130                 135                 140

Ala Lys Gln Pro Leu Asp His Glu Gly Gly Ser Cys Asn Pro Asp Val
145                 150                 155                 160

Arg Leu Arg Gly His Asp Lys Glu Gly Tyr Gly Leu Ser Trp Ser Pro
                165                 170                 175

Phe Lys Glu Gly Phe Leu Leu Ser Gly Ser Asn Asp Gln Lys Ile Cys
                180                 185                 190

Leu Trp Asp Ile Ser Ala Leu Pro Gln Asp Lys Val Leu Met Ala His
            195                 200                 205

His Thr Tyr Glu Glu His Glu Asp Val Val Asp Val Ser Trp His
    210                 215                 220

Pro Lys Asn Glu Asn Leu Phe Gly Ser Val Gly Asp Asp Cys Arg Leu
225                 230                 235                 240

Ile Ile Trp Asp Phe Arg Thr Asn Lys Ala Gln His Ser Val Leu Val
                245                 250                 255

His Glu Lys Glu Val Asn Tyr Leu Ser Phe Asn Ser Tyr Thr Glu Trp
                260                 265                 270

Val Leu Ala Thr Ala Ser Ser Asp Ser Thr Val Gly Leu Phe Asp Met
            275                 280                 285

Arg Lys Leu Ser Ser Pro Leu His Val Phe Gly Ser His Thr Asp Glu
    290                 295                 300

Val Phe Gln Val Glu Trp Asp Pro Asn His Glu Thr Val Leu Ala Ser
305                 310                 315                 320

Ser Gly Gly Asp Arg Arg Leu Met Val Trp Asp Leu Asn Arg Ile Gly
                325                 330                 335

Asp Glu Gln Leu Glu Gly Glu Ala Glu Asp Gly Pro Ser Glu Leu Leu
                340                 345                 350

Phe Ser His Gly Gly His Lys Ala Lys Ile Ser Asp Phe Ser Trp Asn
            355                 360                 365

Lys Asn Glu Pro Trp Val Ile Ser Ser Val Ala Glu Asp Asn Cys Val
    370                 375                 380

Gln Val Trp Gln Met Ala Glu Ser Ile Tyr Arg Glu Asp Asn Asp Asn
385                 390                 395                 400

Gly Asn Cys

<210> SEQ ID NO 3
<211> LENGTH: 403
<212> TYPE: PRT
<213> ORGANISM: Solanum lycopersicum

<400> SEQUENCE: 3

Met Ala Glu Glu Glu Leu Glu Ala Ala Gly Glu Thr Glu Gln Asp Val
1               5                   10                  15

Glu Glu Glu Phe Ala Val Trp Lys Lys Asn Thr Pro Leu Leu Tyr Asp
                20                  25                  30

Leu Val Val Cys His Ala Leu Glu Trp Pro Ser Leu Thr Val Gln Trp
            35                  40                  45

Leu Pro Ser Pro Thr Thr Asp Asp Gly Ala Phe Ala Val His Lys Leu
    50                  55                  60

Ile Leu Gly Thr His Thr Ser Asp Asp Cys Pro Asn Phe Leu Met Val
65                  70                  75                  80

Ala Lys Val His Leu Pro Arg Asn Pro Ala Ser Gly Leu Glu His Asn
                85                  90                  95
```

```
Leu Met Asn Pro Gln Ile Pro Lys Val Glu Ile Val Gln Lys Ile His
            100                 105                 110
Val Asp Gly Glu Val Asn Arg Ala Arg Cys Met Pro Gln Lys Pro Ala
            115                 120                 125
Val Val Ala Ala Lys Thr Ser Ser Glu Val Tyr Val Phe Asp Ser
130                 135                 140
Ala Lys Gln Pro Leu Asp His Glu Gly Gly Ser Cys Asn Pro Asp Val
145                 150                 155                 160
Arg Leu Arg Gly His Asp Lys Glu Gly Tyr Gly Leu Ser Trp Ser Pro
                165                 170                 175
Phe Lys Glu Gly Phe Leu Leu Ser Gly Ser Asn Asp Gln Lys Ile Cys
            180                 185                 190
Leu Trp Asp Ile Ser Ala Leu Pro Gln Asp Lys Val Leu Met Ala His
            195                 200                 205
His Thr Tyr Glu Glu His Glu Asp Val Val Glu Asp Val Ser Trp His
            210                 215                 220
Pro Lys Asn Glu Asn Leu Phe Gly Ser Val Gly Asp Asp Cys Arg Leu
225                 230                 235                 240
Ile Ile Trp Asp Phe Arg Thr Asn Lys Ala Gln His Ser Val Leu Val
                245                 250                 255
His Glu Lys Glu Val Asn Tyr Leu Ser Phe Asn Ser Tyr Thr Glu Trp
            260                 265                 270
Val Leu Ala Thr Ala Ser Ser Asp Ser Thr Val Gly Leu Phe Asp Met
            275                 280                 285
Arg Lys Leu Ser Ser Pro Leu His Val Phe Gly Ser His Thr Asp Glu
            290                 295                 300
Val Phe Gln Val Glu Trp Asp Pro Asn His Glu Thr Val Leu Ala Ser
305                 310                 315                 320
Ser Gly Gly Asp Arg Arg Leu Met Val Trp Asp Leu Asn Arg Ile Gly
                325                 330                 335
Asp Glu Gln Leu Glu Gly Glu Ala Glu Asp Gly Pro Ser Glu Leu Leu
            340                 345                 350
Phe Ser His Gly Gly His Lys Ala Lys Ile Ser Asp Phe Ser Trp Asn
            355                 360                 365
Lys Asn Glu Pro Trp Val Ile Ser Ser Val Ala Glu Asp Asn Cys Val
            370                 375                 380
Gln Val Trp Gln Met Ala Glu Ser Ile Tyr Arg Glu Asp Asn Asp Asn
385                 390                 395                 400
Gly Asn Cys

<210> SEQ ID NO 4
<211> LENGTH: 1212
<212> TYPE: DNA
<213> ORGANISM: Solanum lycopersicum

<400> SEQUENCE: 4
atggctgaag aagaattgga ggcggcggga gaaaccgaac aagatgtaga agaggagttc      60 gccgttttgga agaagaacac gccgttgctc tacgatcttg tcgtttgtca tgcccttgaa    120
tggccttctc tcaccgttca atggcttccg tctccaacca ccgacgacgg tgcttttgct    180
gtacacaagc tcattctcgg aactcacacc tccgacgatt gccccaactt cctcatggtc    240
gcaaaggttc atctccctcg gaatcctgct tcaggacttg aacacaatct catgaatcct    300
caaatcccta aggtagagat agtacaaaag attcatgttg acggagaagt gaatagagcg    360
```

```
agatgtatgc cacagtagcc agctgtagtt gcagctaaga ctagtagctc tgaagtttat      420
gtctttgact cagctaaaca gccccttgat catgaaggtg ggtcttgtaa ccctgatgtt      480
cgacttcgtg ggcatgataa agaaggttat ggcttgtcgt ggagcccgtt aaagagggt      540 tttcttttga gtggttcaaa tgatcagaag atttgtttgt gggatatatc tgcattgcct      600
caagataaag ttcttatggc tcatcatact tatgaggagc atgaagatgt agttgaggat      660
gtgtcatggc atccaaagaa tgagaaccta tttggttctg tcggagatga ttgtcgtctg      720
atcatttggg acttccggac aaacaaagcc caacactcgg ttttagtgca tgagaaagag      780
gtgaattatt tatcttttcaa ctcatatact gaatgggttc ttgctacagc atcgtcagat      840
agtactgttg gtctgttcga catgcgaaag cttagctctc cattgcacgt gtttggcagt      900
catacggatg aggtgttcca ggtagaatgg gatcctaatc atgagactgt actggcatct      960
tcaggtggtg atagaaggtt gatggtctgg gatcttaaca ggattggtga cgagcaattg     1020
gaaggggaag ctgaagacgg accgtcagaa cttcttttct ctcatggcgg tcacaaagca     1080
aagatatctg attttttcatg gaacaagaac gagccatggg tcatttcaag tgtggcagaa     1140
gacaactgtg tccaagtctg gcagatggct gagagcatct accgtgagga caatgacaat     1200
ggcaactgct ga                                                         1212

<210> SEQ ID NO 5
<211> LENGTH: 1212
<212> TYPE: DNA
<213> ORGANISM: Solanum lycopersicum

<400> SEQUENCE: 5
atggctgaag aagaattgga ggcggcggga gaaaccgaac aagatgtaga agaggagttc       60
gccgtttgga agaagaacac gccgttgctc tacgatcttg tcgtttgtca tgcccttgaa      120
tggccttctc tcaccgttca atggcttccg tctccaacca ccgacgacgg tgcttttgct      180
gtacacaagc tcattctcgg aactcacacc tccgacgatt gccccaactt cctcatggtc      240
gcaaaggttc atctccctcg gaatcctgct tcaggacttg aacacaatct catgaatcct      300
caaatcccta aggtagagat agtacaaaag attcatgttg acgagaagt gaatagagcg       360 agatgtatgc cacagaagcc agctgtagtt gcagctaaga ctagtagctc tgaagtttat      420
gtctttgact cagctaaaca gccccttgat catgaaggtg ggtcttgtaa ccctgatgtt      480
cgacttcgtg ggcatgataa agaaggttat ggcttgtcgt ggagcccgtt aaagagggt      540 tttcttttga gtggttcaaa tgatcagaag atttgtttgt gggatatatc tgcattgcct      600
caagataaag ttcttatggc tcatcatact tatgaggagc atgaagatgt agttgaggat      660
gtgtcatggc atccaaagaa tgagaaccta tttggttctg tcggagatga ttgtcgtctg      720
atcatttggg acttccggac aaacaaagcc caacactcgg ttttagtgca tgagaaagag      780
gtgaattatt tatcttttcaa ctcatatact gaatgggttc ttgctacagc atcgtcagat      840
agtactgttg gtctgttcga catgcgaaag cttagctctc cattgcacgt gtttggcagt      900
catacggatg aggtgttcca ggtagaatgg gatcctaatc atgagactgt actggcatct      960
tcaggtggtg atagaaggtt gatggtctgg gatcttaaca ggattggtga cgagcaattg     1020
gaaggggaag ctgaagacgg accgtcagaa cttcttttct ctcatggcgg tcacaaagca     1080
aagatatctg attttttcatg gaacaagaac gagccatggg tcatttcaag tgtggcagaa     1140
gacaactgtg tccaagtctg gcagatggct gagagcatct accgtgagga caatgacaat     1200
```
ggcaactgct ga                                                        1212

<210> SEQ ID NO 6
<211> LENGTH: 125
<212> TYPE: PRT
<213> ORGANISM: Solanum lycopersicum

<400> SEQUENCE: 6

Met Ala Glu Glu Glu Leu Glu Ala Ala Gly Glu Thr Glu Gln Asp Val
1               5                   10                  15

Glu Glu Glu Phe Ala Val Trp Lys Lys Asn Thr Pro Leu Leu Tyr Asp
            20                  25                  30

Leu Val Val Cys His Ala Leu Glu Trp Pro Ser Leu Thr Val Gln Trp
        35                  40                  45

Leu Pro Ser Pro Thr Thr Asp Asp Gly Ala Phe Ala Val His Lys Leu
    50                  55                  60

Ile Leu Gly Thr His Thr Ser Asp Asp Cys Pro Asn Phe Leu Met Val
65                  70                  75                  80

Ala Lys Val His Leu Pro Arg Asn Pro Ala Ser Gly Leu Glu His Asn
                85                  90                  95

Leu Met Asn Pro Gln Ile Pro Lys Val Glu Ile Val Gln Lys Ile His
            100                 105                 110

Val Asp Gly Glu Val Asn Arg Ala Arg Cys Met Pro Gln
        115                 120                 125

<210> SEQ ID NO 7
<211> LENGTH: 1212
<212> TYPE: DNA
<213> ORGANISM: Artificial Sequence
<220> FEATURE:
<223> OTHER INFORMATION: Description of Artificial Sequence: Synthetic
      Solanum consensus Msi2 coding sequence

<400> SEQUENCE: 7
atggcwgaag aagaahtgga ggcggcggga gaaaccgmrc magakgtwga agargagttc      60
gccgtttgga agaagaacac gccgttgctc tacgatcttg tcgtytgtca tgcccttgaa     120
tggccktckc tcacygttca atggcttccr tcyccmacca ccgacgacgg tgcttttgyt     180
gtacacaagm tcatyctcgg mactcacacc tccgaygatt gccccaactt cctcatggtc     240
gcaaakgtys atctcccckcg daatcctgct tcrggactyg aacacaatct cakgaatcct     300
caaatcccta aggtagagat agtrcaaaag attcatgttg ayggagaagt gaatagrgcg     360
agatgtatgc cacagaarcc agctgtagtt gcagchaaga ctagtagckc tgargtttat     420
rtctttgact cagctaaaca rcccyttgat caygaaggtg ggtcttgtaa ccctgatgtt     480
mgacttcgwg ggcaygataa agaaggttat ggcttgtcst ggagccyrtt taargagggt     540
tttcttytga gtggttcaaa ygatcagaag atytgtttst ggratrtatc tgcattgcct     600
cragataaag tkcttatggc ycaycatact tatgaggagc atgaagatgt agttgaggay     660
gtktcatggc ayccaawgaa tgagaaccta tttggytcyg tcggagatga ttgtcgtctg     720
atcatttggg acttvcggac raacaaagcc caacastcdg ttttagygca tgagaaagag     780
gtgaattatt tatctttcaa ytcatatact gartgggtts ttgctacagc atcrtcwgat     840
agtactgttg gtctrtttyga catgcgwaag cttagctctc cattgcaygt gtttggcagt     900
catacggatg aggtrttcca ggtagaatgg gatcctaatc atgaracygt actggcatct     960
tcrggtggtg atagaaggtt gatggtctgg gatcttaaca ggattggtga cgagcaattg    1020

| | |
|---|---|
| gaaggggaag ctgaagaygg rccbtcmgaa cttcttttct ctcatggcgg tcacaaagca | 1080 |
| aaratawctg attttttcrtg gracawkaay gagscatggg tcatytcaag tgtggcagaa | 1140 |
| gacaaytgtg tccaagtctg gcagatggct gagagcatct accgygarga caatgrcaat | 1200 |
| ggcaamtsct ga | 1212 |

<210> SEQ ID NO 8
<211> LENGTH: 2650
<212> TYPE: DNA
<213> ORGANISM: Solanum lycopersicum

<400> SEQUENCE: 8

| | |
|---|---|
| atggctgaag aagaattgga ggcggcggga gaaaccgaac aagatgtaga agaggagttc | 60 |
| gccgttttgga agaagaacac gccgttgctc tacgatcttg tcgtttgtca tgcccttgaa | 120 |
| tggccttctc tcaccgttca atggcttccg tctccaacca ccgacgacgg tgcttttgct | 180 |
| gtacacaagc tcattctcgg aactcacacc tccgacgatt gccccaactt cctcatggtc | 240 |
| gcaaaggttc atcccctcg gaatcctgct tcaggacttg aacacaatct catgaatcct | 300 |
| caaatcccta aggtctgtaa ctccttacaa tcggttaaac tacactaata tttgaaaaaa | 360 |
| ttccctatct gttaaaatgc gctaaatgtg taaaaattag ttacatattt ctatattcgt | 420 |
| gatgagtgat ccatatgtgt acatatatga actgtttgat aaaatatcca atgaagaaa | 480 |
| gttctttgtt aatgaatcaa tttatgaata tgtggtgcct atcggtgttt ctatgaagga | 540 |
| agtttaatct ggaagtattt ttttttcctag tgttaaaacc tgtgaataaa ttggtcaatt | 600 |
| aagtttttct agtgtacaca ggtagagata gtacaaaaga ttcatgttga cggagaagtg | 660 |
| aatagagcga gatgtatgcc acagaagcca gctgtagttg cagctaagac tagtagctct | 720 |
| gaagtttatg tctttgactc agctaaacag ccccttgatc atgaaggtgg gtcttgtaac | 780 |
| cctgatgttc gacttcgtgg gcatgataaa gaaggttatg gcttgtcgtg gagcccgttt | 840 |
| aaagagggtt ttcttttgag tggttcaaat gatcagaaga tttgtttgtg ggatatatct | 900 |
| gcattgcctc aagataaagt tcttatggct catcatactt atgaggtaat gtgatctgtc | 960 |
| cttttcaccca atgtgctgat tcaactgagt ttcttttgtt gattccgtag ttgaatatca | 1020 |
| ctatggcaga tatgaattta attctggtat ttttgtatag gagcatgaag atgtagttga | 1080 |
| ggatgtgtca tggcatccaa agaatgagaa cctatttggt tctgtcggag atgattgtcg | 1140 |
| tctgatcatt tgggacttcc ggacaaacaa agcccaacac tcggttttag tgcatgagaa | 1200 |
| agaggtcagt gtcttcaaat tccatcttgt ttaatatttt accacgcact gtttttatctg | 1260 |
| tatcattgag attaatctct actatgcttg tctaatcgtt caatgatata acccatagat | 1320 |
| catgcactag gcacccaata tggtattaaa gaaaaacata tgaaactatt ggataggact | 1380 |
| gttgagatgt catatgagtc tttgaataat gggacctcca acaatggtta tccttcgtac | 1440 |
| attgtactgg tcttatttttt atctgtttga gaggttaatc ctgtcacctg tttcacatgc | 1500 |
| attaatgaaa tgcgaattca gaaagttaat agcatgtgca ccggctgaac aaacttttct | 1560 |
| caatagttat cctgaggcag tcttgctgat cttgtttttc ttcctctctg caggtgaatt | 1620 |
| atttatcttt caactcatat actgaatggg ttccttgctac agcatcgtca gatagtactg | 1680 |
| ttggtctgtt cgacatgcga aagcttagct ctccattgca cgtgtttggc agtcatacgt | 1740 |
| atgtccttca gcttatttca agtcttcaaa tttgttgtgg tcaatctttt acgtcactcc | 1800 |
| attatttat tggcttggtg actatcgaaa tcacagttta ctgatgttcg tctccagtga | 1860 |
| tgattgactt gtcaatattt ggatcccta gtatgctata cagagctcct tttgaaacaa | 1920 |

| | |
|---|---|
| aaaacttatg aaaactaaaa gtatctgtca aatctactta tcgtggtgca tttctttcat | 1980 |
| cattgttgaa ttattttgcc tgtgtatgca cacagaaatt ggtcaaatct gctgttgctt | 2040 |
| ttgagccctg cttatgctct tactcagcca attcctggtt ttagatgaca ttgctgtagg | 2100 |
| aattctcatg cattcttcta aatgtgacaa ctcttctacc ttttgtttct accaatgata | 2160 |
| cgattttttgt cattaaacct ttttgcaggg atgaggtgtt ccaggtagaa tgggatccta | 2220 |
| atcatgagac tgtactggca tcttcaggtg gtgatagaag gttgatggtc tgggatctta | 2280 |
| acaggtacat catgcatgaa atgaattcca acacgaaa acgatggtgg tggattatca | 2340 |
| gttatcactt aaatttaata cgagataatg gtgatactaa ccaaagaaag agttgtatgg | 2400 |
| tttacctttt ttgtcttaca acaagattgt tgtcttcagg attggtgacg agcaattgga | 2460 |
| aggggaagct gaagacggac cgtcagaact tcttttctct catggcggtc acaaagcaaa | 2520 |
| gatatctgat ttttcatgga acaagaacga gccatgggtc atttcaagtg tggcagaaga | 2580 |
| caactgtgtc caagtctggc agatggctga gagcatctac cgtgaggaca atgacaatgg | 2640 |
| caactgctga | 2650 |

<210> SEQ ID NO 9
<211> LENGTH: 2650
<212> TYPE: DNA
<213> ORGANISM: Solanum lycopersicum

<400> SEQUENCE: 9

| | |
|---|---|
| atggctgaag aagaattgga ggcggcggga gaaaccgaac aagatgtaga agaggagttc | 60 |
| gccgtttgga agaagaacac gccgttgctc tacgatcttg tcgtttgtca tgcccttgaa | 120 |
| tggccttctc tcaccgttca atggcttccg tctccaacca ccgacgacgg tgcttttgct | 180 |
| gtacacaagc tcattctcgg aactcacacc tccgacgatt gccccaactt cctcatggtc | 240 |
| gcaaaggttc atctccctcg gaatcctgct tcaggacttg aacacaatct catgaatcct | 300 |
| caaatcccta aggtctgtaa ctccttacaa tcggttaaac tacactaata tttgaaaaaa | 360 |
| ttccctatct gttaaaatgc gctaatagtg taaaaattag ttacatattt ctatattcgt | 420 |
| gatgagtgat ccatatgtgt acatatatga actgtttgat aaaatatcca aatgaagaaa | 480 |
| gttctttgtt aatgaatcaa tttatgaata tgtggtgcct atcggtgttt ctatgaagga | 540 |
| agtttaatct ggaagtattt ttttttcctag tgttaaaacc tgtgaataaa ttggtcaatt | 600 |
| aagttttttct agtgtacaca ggtagagata gtacaaaaga ttcatgttga cggagaagtg | 660 |
| aatagagcga gatgtatgcc acagtagcca gctgtagttg cagctaagac tagtagctct | 720 |
| gaagtttatg tctttgactc agctaaacag cccccttgatc atgaaggtgg gtcttgtaac | 780 |
| cctgatgttc gacttcgtgg gcatgataaa gaaggttatg gcttgtcgtg gagcccgttt | 840 |
| aaagagggtt ttcttttgag tggttcaaat gatcagaaga tttgtttgtg ggatatatct | 900 |
| gcattgcctc aagataaagt tcttatggct catcatactt atgaggtaat gtgatctgtc | 960 |
| ctttcaccca atgtgctgat tcaactgagt ttcttttgtt gattccgtag ttgaatatca | 1020 |
| ctatggcaga tatgaattta attctggtat ttttgtatag gagcatgaag atgtagttga | 1080 |
| ggatgtgtca tggcatccaa agaatgagaa cctatttggt tctgtcggag atgattgtcg | 1140 |
| tctgatcatt tgggacttcc ggacaaacaa agcccaacac tcggttttag tgcatgagaa | 1200 |
| agaggtcagt gtcttcaaat tccatcttgt ttaatatttt accacgcact gttttatctg | 1260 |
| tatcattgag attaatctct actatgcttg tctaatcgtt caatgatata acccatagat | 1320 |

```
catgcactag gcacccaata tggtattaaa gaaaaacata tgaaactatt ggataggact    1380
gttgagatgt catatgagtc tttgaataat gggacctcca acaatggtta tccttcgtac    1440
attgtactgg tcttattttt atctgtttga gaggttaatc ctgtcacctg tttcacatgc    1500
attaatgaaa tgcgaattca gaaagttaat agcatgtgca ccggctgaac aaacttttct    1560
caatagttat cctgaggcag tcttgctgat cttgttttc ttcctctctg caggtgaatt     1620
atttatcttt caactcatat actgaatggg ttcttgctac agcatcgtca gatagtactg    1680
ttggtctgtt cgacatgcga aagcttagct ctccattgca cgtgtttggc agtcatacgt    1740
atgtccttca gcttatttca agtcttcaaa tttgttgtgg tcaatctttt acgtcactcc    1800
attattttat tggcttggtg actatcgaaa tcacagttta ctgatgttcg tctccagtga    1860
tgattgactt gtcaatattt ggatcccta gtatgctata cagagctcct tttgaaacaa     1920
aaaacttatg aaaactaaaa gtatctgtca aatctactta tcgtggtgca tttctttcat    1980
cattgttgaa ttattttgcc tgtgtatgca cacagaaatt ggtcaaatct gctgttgctt    2040
ttgagccctg cttatgctct tactcagcca attcctggtt ttagatgaca ttgctgtagg    2100
aattctcatg cattcttcta aatgtgacaa ctcttctacc ttttgtttct accaatgata    2160 cgattttgt cattaaacct ttttgcaggg atgaggtgtt ccaggtagaa tgggatccta     2220
atcatgagac tgtactggca tcttcaggtg gtgatagaag gttgatggtc tgggatctta    2280
acaggtacat catgcatgaa atgaattcca caacacgaaa acgatggtgg tggattatca    2340
gttatcactt aaatttaata cgagataatg gtgatactaa ccaaagaaag agttgtatgg    2400 tttaccttt ttgtcttaca acaagattgt tgtcttcagg attggtgacg agcaattgga     2460
aggggaagct gaagacggac cgtcagaact tcttttctct catggcggtc acaaagcaaa    2520
gatatctgat ttttcatgga acaagaacga gccatgggtc atttcaagtg tggcagaaga    2580
caactgtgtc caagtctggc agatggctga gagcatctac cgtgaggaca atgacaatgg    2640
caactgctga                                                           2650
```

<210> SEQ ID NO 10
<211> LENGTH: 403
<212> TYPE: PRT
<213> ORGANISM: Artificial Sequence
<220> FEATURE:
<223> OTHER INFORMATION: Description of Artificial Sequence: Synthetic
      Solanaceae consensus Msi2 protein sequence
<220> FEATURE:
<221> NAME/KEY: MOD_RES
<222> LOCATION: (35)..(35)
<223> OTHER INFORMATION: Any naturally occurring amino acid
<220> FEATURE:
<221> NAME/KEY: MOD_RES
<222> LOCATION: (54)..(54)
<223> OTHER INFORMATION: Any naturally occurring amino acid
<220> FEATURE:
<221> NAME/KEY: MOD_RES
<222> LOCATION: (58)..(58)
<223> OTHER INFORMATION: Any naturally occurring amino acid
<220> FEATURE:
<221> NAME/KEY: MOD_RES
<222> LOCATION: (74)..(74)
<223> OTHER INFORMATION: Any naturally occurring amino acid
<220> FEATURE:
<221> NAME/KEY: MOD_RES
<222> LOCATION: (189)..(189)
<223> OTHER INFORMATION: Any naturally occurring amino acid
<220> FEATURE:
<221> NAME/KEY: MOD_RES
<222> LOCATION: (199)..(199)
<223> OTHER INFORMATION: Any naturally occurring amino acid
<220> FEATURE:

```
<221> NAME/KEY: MOD_RES
<222> LOCATION: (270)..(270)
<223> OTHER INFORMATION: Any naturally occurring amino acid
<220> FEATURE:
<221> NAME/KEY: MOD_RES
<222> LOCATION: (398)..(398)
<223> OTHER INFORMATION: Any naturally occurring amino acid
<220> FEATURE:
<221> NAME/KEY: MOD_RES
<222> LOCATION: (402)..(402)
<223> OTHER INFORMATION: Any naturally occurring amino acid

<400> SEQUENCE: 10
```

| | | | | | | | | | | | | | |
|---|---|---|---|---|---|---|---|---|---|---|---|---|---|
| Met | Ala | Glu | Glu | Glu | Met | Glu | Ala | Ala | Gly | Glu | Thr | Glu | Gln | Glu | Val |
| 1 | | | | 5 | | | | | 10 | | | | | 15 |

| Glu | Glu | Glu | Phe | Ala | Val | Trp | Lys | Lys | Asn | Thr | Pro | Leu | Leu | Tyr | Asp |
| | | | 20 | | | | | 25 | | | | | 30 | | |

| Leu | Val | Xaa | Cys | His | Ala | Leu | Glu | Trp | Pro | Ser | Leu | Thr | Val | Gln | Trp |
| | | 35 | | | | | 40 | | | | | 45 | | | |

| Leu | Pro | Ser | Pro | Thr | Xaa | Asp | Asp | Gly | Xaa | Phe | Ala | Val | His | Lys | Leu |
| 50 | | | | | 55 | | | | | 60 | | | | | |

| Ile | Leu | Gly | Thr | His | Thr | Ser | Asp | Asp | Xaa | Pro | Asn | Phe | Leu | Met | Val |
| 65 | | | | | 70 | | | | | 75 | | | | | 80 |

| Ala | Asn | Val | His | Leu | Pro | Arg | Asn | Pro | Ala | Ser | Gly | Leu | Glu | His | Asn |
| | | | | 85 | | | | | 90 | | | | | 95 | |

| Leu | Met | Asn | Pro | Gln | Ile | Pro | Lys | Val | Glu | Ile | Val | Gln | Lys | Ile | His |
| | | | 100 | | | | | 105 | | | | | 110 | | |

| Val | Asp | Gly | Glu | Val | Asn | Arg | Ala | Arg | Cys | Met | Pro | Gln | Lys | Pro | Ala |
| | | 115 | | | | | 120 | | | | | 125 | | | |

| Val | Val | Ala | Ala | Lys | Thr | Ser | Ser | Glu | Val | Tyr | Val | Phe | Asp | Ser |
| 130 | | | | | 135 | | | | | 140 | | | | | |

| Ala | Lys | Gln | Pro | Leu | Asp | His | Glu | Gly | Gly | Ser | Cys | Asn | Pro | Asp | Val |
| 145 | | | | | 150 | | | | | 155 | | | | | 160 |

| Arg | Leu | Arg | Gly | His | Asp | Lys | Glu | Gly | Tyr | Gly | Leu | Ser | Trp | Ser | Pro |
| | | | | 165 | | | | | 170 | | | | | 175 | |

| Phe | Lys | Glu | Gly | Phe | Leu | Leu | Ser | Gly | Ser | Asn | Asp | Xaa | Lys | Ile | Cys |
| | | | 180 | | | | | 185 | | | | | 190 | | |

| Leu | Trp | Asp | Val | Ser | Ala | Xaa | Pro | Gln | Asp | Lys | Val | Leu | Met | Ala | His |
| | | | 195 | | | | | 200 | | | | | 205 | | |

| His | Thr | Tyr | Glu | Glu | His | Glu | Asp | Val | Val | Glu | Asp | Val | Ser | Trp | His |
| | 210 | | | | | 215 | | | | | 220 | | | | |

| Pro | Lys | Asn | Glu | Asn | Leu | Phe | Gly | Ser | Val | Gly | Asp | Asp | Cys | Arg | Leu |
| 225 | | | | | 230 | | | | | 235 | | | | | 240 |

| Ile | Ile | Trp | Asp | Leu | Arg | Thr | Asn | Lys | Ser | Gln | His | Ser | Val | Leu | Val |
| | | | | 245 | | | | | 250 | | | | | 255 | |

| His | Glu | Lys | Glu | Val | Asn | Tyr | Leu | Ser | Phe | Asn | Ser | Tyr | Xaa | Glu | Trp |
| | | | 260 | | | | | 265 | | | | | 270 | | |

| Val | Leu | Ala | Thr | Ala | Ser | Ser | Asp | Ser | Thr | Val | Gly | Leu | Phe | Asp | Met |
| | | | 275 | | | | | 280 | | | | | 285 | | |

| Arg | Lys | Leu | Ser | Ser | Pro | Leu | His | Val | Phe | Gly | Ser | His | Thr | Asp | Glu |
| | 290 | | | | | 295 | | | | | 300 | | | | |

| Val | Phe | Gln | Val | Glu | Trp | Asp | Pro | Asn | His | Glu | Thr | Val | Leu | Ala | Ser |
| 305 | | | | | 310 | | | | | 315 | | | | | 320 |

| Ser | Gly | Gly | Asp | Arg | Arg | Leu | Met | Val | Trp | Asp | Leu | Asn | Arg | Ile | Gly |
| | | | | 325 | | | | | 330 | | | | | 335 | |

| Asp | Glu | Gln | Leu | Glu | Gly | Glu | Ala | Glu | Asp | Gly | Pro | Ser | Glu | Leu | Leu |
| | | | 340 | | | | | 345 | | | | | 350 | | |

```
Phe Ser His Gly Gly His Lys Ala Lys Ile Ser Asp Phe Ser Trp Asn
        355                 360                 365

Lys Asn Glu Pro Trp Val Ile Ser Ser Val Ala Glu Asp Asn Cys Val
    370                 375                 380

Gln Val Trp Gln Met Ala Glu Ser Ile Tyr Arg Glu Asp Xaa Asp Asn
385                 390                 395                 400

Gly Xaa Cys
```